(12) United States Patent
Karo et al.

(10) Patent No.: US 7,794,405 B2
(45) Date of Patent: Sep. 14, 2010

(54) CUFF FOR BLOOD PRESSURE MONITOR, AND BLOOD PRESSURE MONITOR HAVING THE SAME

(75) Inventors: Hiromichi Karo, Kyoto (JP); Yoshihiko Sano, Kyoto (JP); Hiroshi Kishimoto, Kyoto (JP); Yoshinori Tsurumi, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 1303 days.

(21) Appl. No.: 11/305,257

(22) Filed: Dec. 19, 2005

(65) Prior Publication Data
US 2006/0135873 A1 Jun. 22, 2006

(30) Foreign Application Priority Data
Dec. 20, 2004 (JP) .............................. 2004-368130

(51) Int. Cl.
*A61B 5/02* (2006.01)
(52) U.S. Cl. .................... 600/499; 600/485; 600/490
(58) Field of Classification Search ................ 600/481, 600/485, 490–499; 428/34.1–36.92; 606/201–203
See application file for complete search history.

(56) References Cited

U.S. PATENT DOCUMENTS

| | | | | |
|---|---|---|---|---|
| 2,307,902 A | * | 1/1943 | Vogt et al. ............... | 383/106 |
| 6,413,224 B1 | * | 7/2002 | Ogura et al. .............. | 600/493 |
| 6,527,727 B2 | * | 3/2003 | Itonaga et al. ............ | 600/499 |
| 6,758,821 B2 | * | 7/2004 | Itonaga et al. ............ | 600/499 |
| 6,866,636 B2 | * | 3/2005 | Inoue et al. .............. | 600/499 |
| 2004/0186385 A1 | | 9/2004 | Mochizuki | |
| 2005/0258061 A1 | * | 11/2005 | Vandecruys et al. ...... | 206/449 |
| 2007/0104905 A1 | * | 5/2007 | Floyd, Jr. ................. | 428/36.1 |
| 2009/0163824 A1 | * | 6/2009 | Ide et al. ................. | 600/499 |

FOREIGN PATENT DOCUMENTS

| | | |
|---|---|---|
| EP | 1-125-551 A2 | 8/2001 |
| EP | 1-374-762 A1 | 1/2004 |
| JP | 02-107226 | 4/1990 |
| JP | 11-299746 A | 11/1999 |
| JP | 2001-224558 | 8/2001 |
| RU | 2 129 833 | 5/1999 |
| TW | 564168 | 12/2003 |

OTHER PUBLICATIONS

Russian Decision on Grant dated May 30, 2007, directed at counterpart RU application No. 2005139788/14.

* cited by examiner

*Primary Examiner*—Patricia C Mallari
*Assistant Examiner*—Karen E Toth
(74) *Attorney, Agent, or Firm*—Morrison & Foerster LLP

(57) ABSTRACT

A cuff for a blood pressure monitor has an air bag inflated/deflated as the air comes in/out. The air bag has an inner wall portion located on the inner side in the fitted state of the cuff and an outer wall portion located outer than the inner wall portion, and a side wall portion connecting side end portions of the inner and outer wall portions and folded inwards in the deflated state of the air bag to form a gusset at each side end portion of the air bag. A bonded portion is provided at a region of the air bag in its winding direction around the living body, for reducing expansion of the gusset formed by the side wall portion. Thus, occurrence of lateral displacement of the cuff is prevented, and a highly reliable blood pressure monitor of high performance can be obtained.

8 Claims, 27 Drawing Sheets

CUFF FOR BLOOD PRESSURE MONITOR, AND BLOOD PRESSURE MONITOR HAVING THE SAME

BACKGROUND OF THE INVENTION

1. Field of the Invention

The present invention relates to a cuff for a blood pressure monitor having a fluid bag for pressing a living body for avascularization of an artery, and a blood pressure monitor provided with the same.

2. Description of the Background Art

Generally, to measure a blood pressure value, a cuff provided with a fluid bag for pressing an artery located within a living body is wound around the body surface, and arterial pressure pulse waves caused in the artery by inflation/deflation of the fluid bag are detected to measure the blood pressure value. Here, the cuff refers to a band-shaped structure having a bladder, which can be wound around a part of a living body, for use in measurement of arterial pressure of an upper limb, a lower limb or the like by introducing fluid such as gas or liquid into the bladder. Thus, the cuff represents the concept including the fluid bag as well as members for winding the fluid bag around the living body. Particularly, the cuff wound around and fitted on a wrist or an upper arm is also called an arm band or a manchette.

Recently, blood pressure monitors are often used not only in medical treatment facilities such as hospitals but also in the households as an apparatus for checking the physical conditions day by day. As such, there are strong demands for improvement in handling of the blood pressure monitors, particularly for ease in fitting operation. To this end, downsizing of the cuff has been attempted. To downsize the cuff, it is necessary to narrow the cuff in the width direction (i.e., direction parallel to the axial direction of the measurement site (e.g., wrist, upper arm or the like) to which the cuff is applied).

To narrow the width of the cuff for the blood pressure monitor, it is important to ensure that the artery is sufficiently pressed for avascularization. In the case of using a cuff for a blood pressure monitor having a large width, a long length in the axial direction of the measurement site covered by the cuff can be guaranteed, which enables sufficient pressing and avascularization of the artery. However, if the width of the cuff is narrowed, the length in the axial direction of the measurement site covered by the cuff becomes short, in which case it would be difficult to sufficiently press the artery for avascularization.

A cuff for a blood pressure monitor disclosed in Japanese Patent Laying-Open No. 02-107226 and a cuff for a blood pressure monitor disclosed in Japanese Patent Laying-Open No. 2001-224558, for example, are known as those directed to prevent degradation of avascularization performance in association with a decreased cuff width. In each of the cuffs for a blood pressure monitor disclosed in these publications, an air bag identified as a fluid bag arranged inside the cuff is provided with a gusset at each side end portion in the width direction. When the air bag is inflated, the gussets expand to make the air bag inflated more uniformly in the width direction. With this configuration, it is possible to sufficiently press the artery for avascularization, not only at the central portion of the cuff, but also at and around the respective side end portions thereof. This ensures accurate measurement of the blood pressure value even if the cuff is narrowed in width.

When the gusset is provided at each side end portion in the width direction of the air bag, however, the side end portion in the width direction of the air bag increases in height in the thickness direction when the air bag is inflated. This may induce lateral displacement of the air bag as will be described below.

FIG. 27 is a schematic diagram showing the state where a typical wrist blood pressure monitor is mounted on a measurement site of the wrist. FIG. 28 is a schematic cross sectional view of the cuff for the blood pressure monitor shown in FIG. 27, taken along the line XXVIII-XXVIII in FIG. 27. FIG. 29 is a schematic diagram showing the state where there occurs lateral displacement of the cuff for the wrist blood pressure monitor in the measurement state shown in FIG. 27. FIG. 30 is a schematic cross sectional view of the cuff for a blood pressure monitor and the wrist shown in FIG. 29, taken along the line XXX-XXX in FIG. 29.

As shown in FIG. 27, the wrist blood pressure monitor 100 includes a main body 110 and a cuff 130. Upon measurement of blood pressure values using wrist blood pressure monitor 100, cuff 130 of blood pressure monitor 100 is wound around the wrist 300 as the measurement site in the circumferential direction. As shown in FIG. 28, cuff 130 primarily includes a cover member 140 in a bag shape, and an air bag 150 and a curled elastic member 170 arranged inside cover member 140. Curled elastic member 170 is elastic and curved to temporarily fit the cuff on the wrist. Cover member 140, air bag 150 and curled elastic member 170 extend with their longitudinal direction corresponding to the winding direction of cuff 130.

Cover member 140 is formed into a bag shape by laying an inner cover 141 made of highly elastic cloth or the like and an outer cover 142 made of less elastic cloth or the like one on the other and connecting their rims. Air bag 150 is formed into a bag shape by laying a resin sheet 152 constituting an inner wall portion located on the wrist side in the fitted state of the cuff and a resin sheet 151 constituting an outer wall portion located on the outer side than the inner wall portion one on the other and melting and bonding their rims, and has an inflated/deflated space 166 therein. Resin sheet 152 constituting the inner wall portion of air bag 150 has its side end portions folded and melted and bonded to resin sheet 151 constituting the outer wall portion, so that gussets are formed at the respective side wall portions of air bag 150. On the outer peripheral surface of air bag 150, curled elastic member 170 identified as an elastic member, which is wound annularly and changeable in size in a radial direction, is attached using an attaching member such as a double-faced tape 181.

In wrist blood pressure monitor 100 of the above configuration, a pump, a valve and the like identified as an inflating/deflating portion arranged inside main body 110 are used to increase or decrease the pressure within inflated/deflated space 166 of air bag 150 arranged inside cuff 130 to inflate or deflate air bag 150. The blood pressure value is calculated based on the pressure information detected during inflation/deflation of air bag 150.

In the state where air bag 150 is inflated, if an external force is applied to outer cover 142 of cover member 140 in the direction parallel to the axial direction of wrist 300, the outer portion of cuff 130 may suffer lateral displacement in the axial direction of wrist 300, whereas the inner portion of cuff 130 will not suffer lateral displacement since it is in contact with wrist 300. This causes a part of cuff 130 to protrude as shown by a reference character 190 in FIG. 29. Even if there is no external force applied, pressure balance of air bag 150 may be lost due to the inclined shape of the surface of wrist 300, which may cause lateral displacement as well.

As shown in FIG. 30, the lateral displacement described above occurs as the pressure balance of air bag 150 is lost at the time of inflation, causing movement of curled elastic member 170, outer cover 142 and resin sheet 151 as a whole in the axial direction of wrist 300. When curled elastic member 170 moves in the axial direction of wrist 300, the air in air bag 150 moves toward the end portion of air bag 150 opposite to the moved direction of curled elastic member 170, which causes deformation of air bag 150, leading to occurrence of the protruding portion 190 described above. When such protruding portion 190 is generated, it is not possible to efficiently and uniformly press air bag 150 against wrist 300, in which case sufficient avascularization performance cannot be obtained, resulting in deterioration of measurement accuracy. Further, the both ends (regions A shown in FIG. 30) of the attached portion of air bag 150 and curled elastic member 170 would suffer a force in the direction causing peeling of air bag 150 from curled elastic member 170, which may degrade reliability of the attached portion.

The lateral displacement described above is more likely to occur as the thickness of inflated/deflated space 166 is greater with respect to the width of air bag 150 at the time of inflation. It poses a serious problem especially in the configuration where gussets are formed at both side end portions of air bag 150 for the purposes of preventing degradation of measurement accuracy attributable to reduction in width of cuff 130. The above problem however is not restricted to the cuff for a blood pressure monitor having such a configuration. A cuff for a blood pressure monitor not provided with the gussets at the side end portions of the air bag would also suffer the problem to some extent, for which a solution is sought.

SUMMARY OF THE INVENTION

An object of the present invention is to provide a cuff for a blood pressure monitor capable of preventing lateral displacement of the cuff, and to thereby implement a highly reliable blood pressure monitor of high performance.

A cuff for a blood pressure monitor according to a first aspect of the present invention has a fluid bag inflated and deflated as a fluid comes in and out. The fluid bag includes an inner wall portion located on an inner side in the state where the cuff for a blood pressure monitor is wound around a living body, an outer wall portion located on an outer side than the inner wall portion, and a side wall portion connecting a side end portion of the inner wall portion and a side end portion of the outer wall portion and folded inwards in a width direction of the fluid bag in a deflated state where the fluid bag is not pressurized to thereby form a gusset at a side end portion of the fluid bag. A joined portion for reducing expansion of the gusset formed by the side wall portion is provided at a region of the side end portion of the fluid bag in its winding direction around the living body.

As such, by forming the joined portion for reducing expansion of the gusset formed by the side wall portion in a region of the fluid bag in its winding direction around the living body, a change in shape of the side end portion of the fluid bag is restricted by the presence of the joined portion, and accordingly, it is possible to prevent lateral displacement of the fluid bag and uniform distribution of the pressing force over the measurement site is realized. Accordingly, it is possible to provide a highly reliable cuff for a blood pressure monitor, and the blood pressure value can be measured with high precision. It is noted that "reducing expansion of the gusset" herein not only refers to making the expansion of the gusset smaller than in the other region, but also refers to completely eliminating the gusset in the relevant region.

In the cuff for a blood pressure monitor according to the first aspect of the present invention, it is preferable that the joined portion is formed by joining wall surfaces of the side wall portion that would face each other in the state where the side wall portion is folded. Alternatively, the joined portion may be formed by joining a wall surface of the side wall portion with a wall surface of the outer wall portion that the wall surface of the side wall portion would face in the state where the side wall portion is folded, or may be formed by joining a wall surface of the side wall portion with a wall surface of the inner wall portion that the wall surface of the side wall portion would face in the state where the side wall portion is folded.

With such configuration, the joined portion can be formed in a simple manner.

In the cuff for a blood pressure monitor according to the first aspect of the present invention, it is preferable that the fluid bag further has a connecting portion located between the inner wall portion and the outer wall portion inside the fluid bag and connecting a pair of side wall portions located at the respective side end portions of the fluid bag.

With this configuration, when the fluid bag changes from the inflated state to the deflated state, the side wall portions serving as the gussets are surely folded inwards in place. This ensures that the fluid bag repeatedly alters its shape as appropriate in a stable manner when inflated/deflated.

In the cuff for a blood pressure monitor according to the first aspect of the present invention, it is preferable that the joined portion is located approximately at a central portion of the fluid bag in its winding direction around the living body.

With this configuration, a change in shape of the fluid bag is restricted at the central portion in the winding direction around the living body where lateral displacement is most likely to occur. Accordingly, it is possible to effectively prevent the lateral displacement.

In the cuff for a blood pressure monitor according to the first aspect of the present invention, it is preferable that joining in the joined portion is performed by melting and bonding.

Thus, by employing melting and bonding, the joined portion can readily be formed.

A cuff for a blood pressure monitor according to a second aspect of the present invention has a fluid bag inflated and deflated as a fluid comes in and out. The fluid bag includes an inner wall portion located on an inner side in the state where the cuff for a blood pressure monitor is wound around a living body, an outer wall portion located on an outer side than the inner wall portion, a side wall portion connecting a side end portion of the inner wall portion and a side end portion of the outer wall portion and folded inwards in a width direction of the fluid bag in a deflated state where the fluid bag is not pressurized to thereby form a gusset at a side end portion of the fluid bag, and a connecting portion located between the inner wall portion and the outer wall portion inside the fluid bag and connecting a pair of side wall portions located at the respective side end portions of the fluid bag. A joined portion is provided at a region of the fluid bag in its winding direction around the living body. The joined portion is formed by joining a wall surface of the connecting portion with a part of a wall surface of the fluid bag located on the side of the inner wall portion or on the side of the outer wall portion when seen from the connecting portion.

With this configuration, in the inflated state of the fluid bag, displacement between the inner wall portion and the connecting portion in the width direction of the fluid bag is unlikely to occur, and thus, lateral displacement of the fluid bag can be prevented. Accordingly, it is possible to provide a highly reliable cuff for a blood pressure monitor, and the blood pressure value can be measured with high precision.

In the cuff for a blood pressure monitor according to the second aspect of the present invention, it is preferable that the joined portion is located approximately at a central portion of the fluid bag in its winding direction around the living body.

With this configuration, a change in shape of the fluid bag is restricted in the central portion in the winding direction around the living body where lateral displacement is most likely to occur, and accordingly, the lateral displacement can be prevented effectively.

In the cuff for a blood pressure monitor according to the second aspect of the present invention, it is preferable that joining in the joined portion is performed by melting and bonding.

Thus, by employing melting and bonding, the joined portion can readily be formed.

A blood pressure monitor according to the present invention includes: any of the cuffs for a blood pressure monitor described above; an inflating/deflating portion for inflating and deflating the fluid bag; a pressure detecting portion for detecting a pressure in the fluid bag; and a blood pressure value calculating portion for calculating a blood pressure value based on pressure information detected by the pressure detecting portion.

With this configuration, it is possible to provide a highly reliable blood pressure monitor of high performance.

According to the present invention, in a cuff for a blood pressure monitor, occurrence of the lateral displacement as described above can be prevented, and uniform distribution of the pressing force over the measurement site is assured. Accordingly, a highly reliable blood pressure monitor of high performance can be implemented.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, an embodiment of the present invention will be described in detail with reference to the drawings. In the embodiment below, a wrist blood pressure monitor will be described as an example of the blood pressure monitor.

Figure 1:
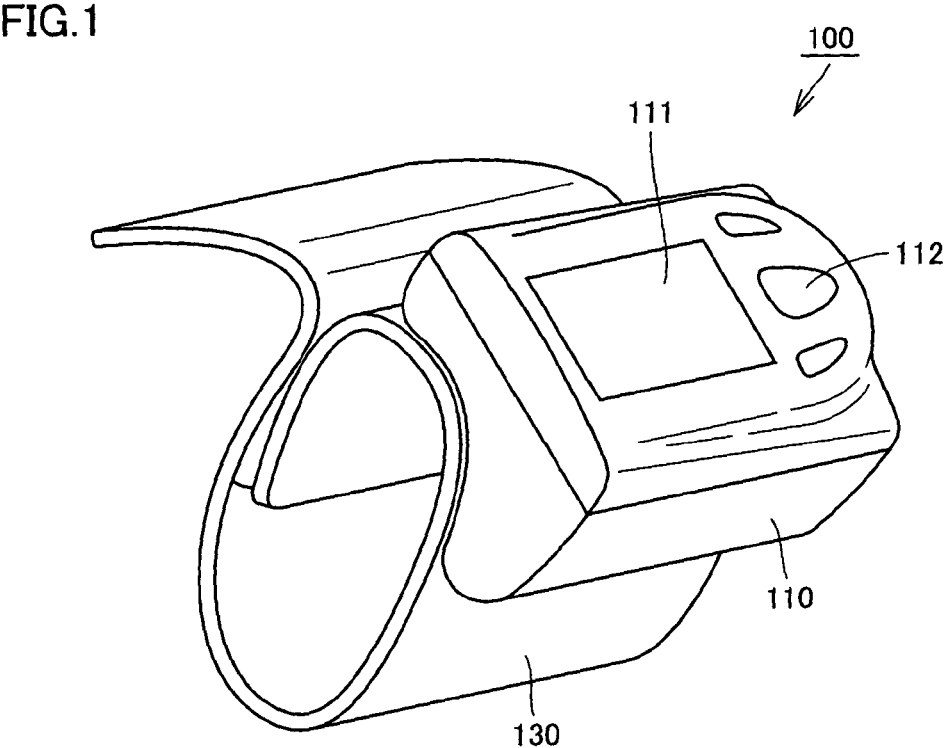
FIG. 1 is a perspective view of a blood pressure monitor according to an embodiment of the present invention.

FIG. 1 is a perspective view of a blood pressure monitor according to the embodiment of the present invention. As shown in FIG. 1, the blood pressure monitor 100 of the embodiment of the present invention includes a main body 110 and a cuff 130. A display portion 111 and a manipulation portion 112 are arranged on the surface of main body 110. Cuff 130 is attached to main body 110.

Figure 2:
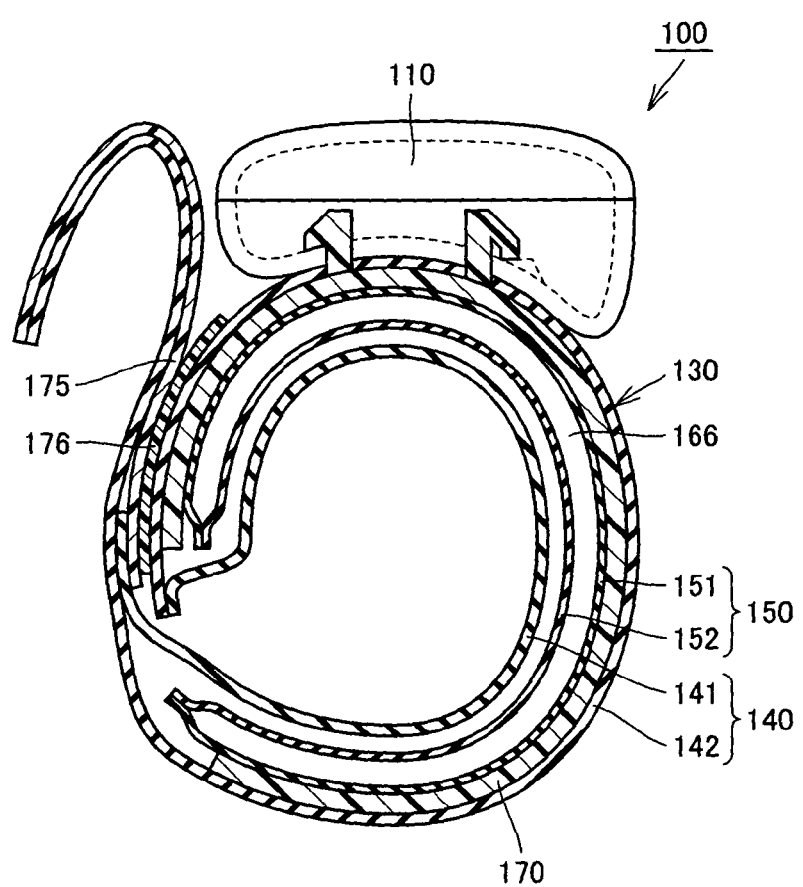
FIG. 2 is a vertical cross sectional view showing an inner structure of a cuff for the blood pressure monitor according to the embodiment of the present invention.

FIG. 2 is a vertical cross sectional view showing an inner structure of the cuff for the blood pressure monitor shown in FIG. 1. As shown in FIG. 2, cuff 130 for the blood pressure monitor of the present embodiment primarily includes a cover member 140 of a bag shape that is made of highly elastic cloth or the like, an air bag 150 identified as a fluid bag that is arranged inside cover member 140, and a curled elastic member 170 that is arranged inside cover member 140 on an outer side of air bag 150 in the fitted state of the cuff. Cover member 140, air bag 150 and curled elastic member 170 extend with their longitudinal direction corresponding to the winding direction of cuff 130.

Cover member 140 has an inner cover 141 positioned on the inner side in the fitted state, and an outer cover 142 positioned on the outer side than inner cover 141. Inner cover 141 and outer cover 142 are laid one on the other and their rims are coupled to form a bag shape. On one end in the longitudinal direction of cover member 140, a velcro fastener 175 is provided on the inner peripheral surface. On the other end in the longitudinal direction of cover member 140, a velcro fastener 176 for engagement with velcro fastener 175 is attached to the outer peripheral surface. Velcro fasteners 175, 176 are members for securing blood pressure monitor 100 on the measurement site of the wrist in a stable manner when cuff 130 is mounted on the wrist.

Air bag 150 is made of a member of a bag shape that is formed using resin sheets. For example, in an air bag 150A contained in a cuff 130 for a blood pressure monitor according to Example 1 based on the present embodiment as will be described later, a resin sheet 152 constituting an inner wall portion located on the wrist side in the state where cuff 130 is wound around the wrist and a resin sheet 151 constituting an outer wall portion located on the outer side than the inner wall portion are laid one on the other and their rims are melted and bonded to form a bag shape, which has an inflated/deflated space 166 therein (for details, see Example 1 below). Inflated/deflated space 166 is connected via a tube 120 to an air system 121 for blood pressure measurement of main body 110, which will be described later (see FIG. 3).

As the material for the resin sheets constituting air bag 150, any material can be used as long as it exhibits excellent elasticity and prevents leakage of the air from inflated/deflated space 166 after melting and bonding. From these standpoints, optimal materials for the resin sheets include copolymer of ethylene-vinyl acetate (EVA), soft polyvinyl chloride (PVC), polyurethane (PU), crude rubber, and the like.

On the outer side of air bag 150, curled elastic member 170 identified as an elastic member is arranged, which is wound in an annular shape and elastically deformable in a radial direction. Curled elastic member 170 is attached to the outer peripheral surface of air bag 150 using an attaching member such as a double-faced tape (not shown). Curled elastic member 170 is configured to maintain its own annular shape corresponding to the contour of the wrist, and facilitates fitting of cuff 130 on the measurement site by the subject himself/herself. Curled elastic member 170 is made of a resin member of polypropylene or the like, so as to exert sufficient elastic force.

Figure 3:
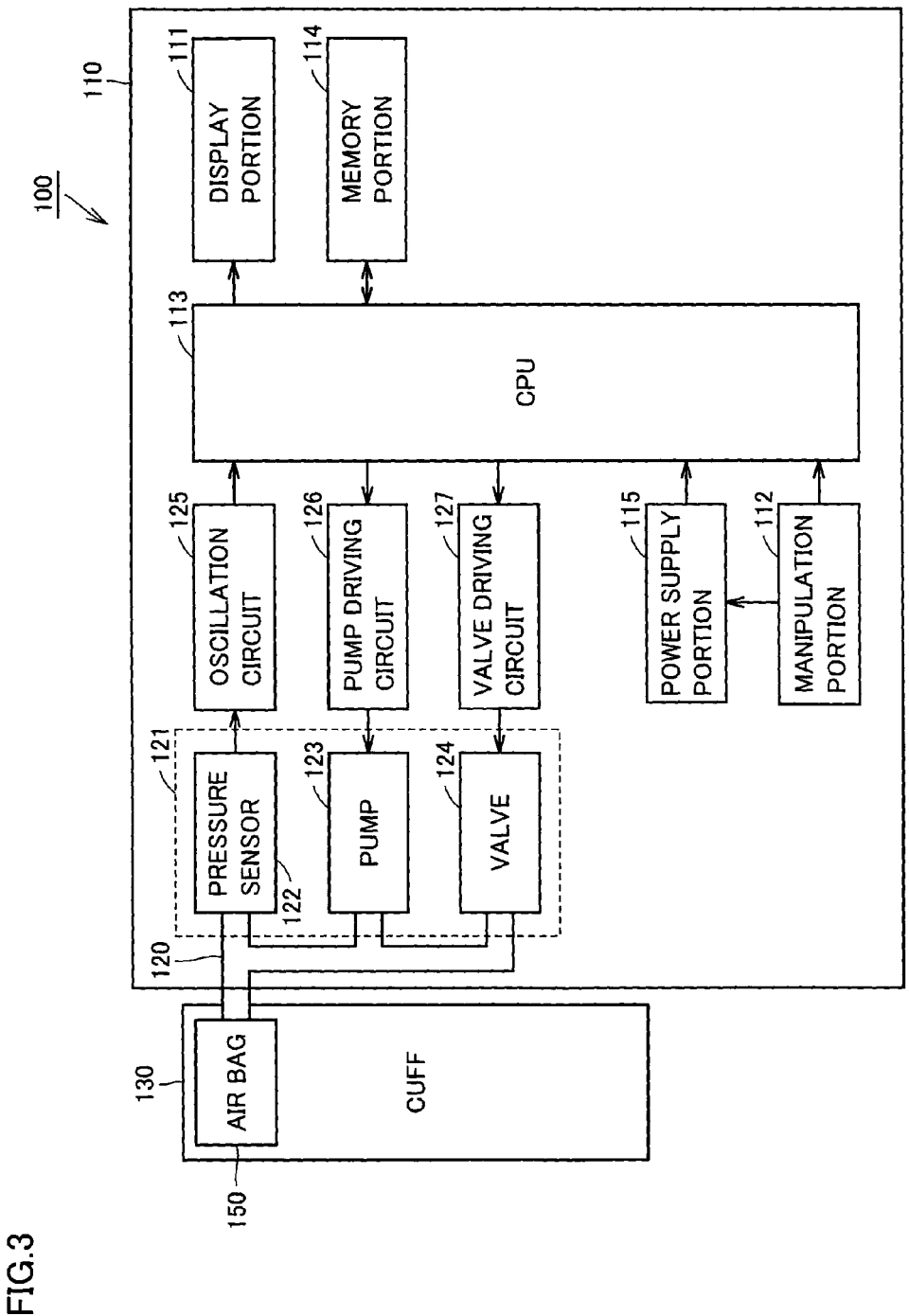
FIG. 3 is a block diagram showing a configuration of the blood pressure monitor according to the embodiment of the present invention.

FIG. 3 is a block diagram showing a configuration of the blood pressure monitor according to the present embodiment. As shown in FIG. 3, main body 110 includes an air system 121 for blood pressure measurement for supplying and evacuating the air to and from air bag 150 via a tube 120, and an oscillation circuit 125, a pump driving circuit 126 and a valve driving circuit 127 which are provided in association with air system 121 for blood pressure measurement. These components function as an inflating/deflating portion for inflating and deflating air bag 150.

Main body 110 further includes a CPU (Central Processing Unit) 113 for controlling and monitoring the respective portions in a centralized manner, a memory portion 114 for storing a program for causing CPU 113 to conduct a prescribed operation and various information including blood pressure values measured, a display portion 111 for displaying the information including a blood pressure measurement result, a manipulation portion 112 manipulated for inputting various instructions for measurement, and a power supply portion 115 for supplying electric power to CPU 113 by an instruction of power ON from manipulation portion 112. CPU 113 serves as a blood pressure value calculating portion for calculating a blood pressure value.

Air system 121 for blood pressure measurement has a pressure sensor 122 having an output value changed in accordance with the pressure within air bag 150 (hereinafter, referred to as "cuff pressure"), a pump 123 for supplying the air to air bag 150, and a valve 124 that is opened or closed to evacuate the air from or seal the air in air bag 150. Pressure sensor 122 serves as a pressure detecting portion for detecting the cuff pressure. Oscillation circuit 125 outputs to CPU 113 a signal of oscillation frequency corresponding to the output value of pressure sensor 122. Pump driving circuit 126 controls driving of pump 123 based on a control signal supplied from CPU 113. Valve driving circuit 127 controls opening/closing of valve 124 based on a control signal supplied from CPU 113.

Figure 4:
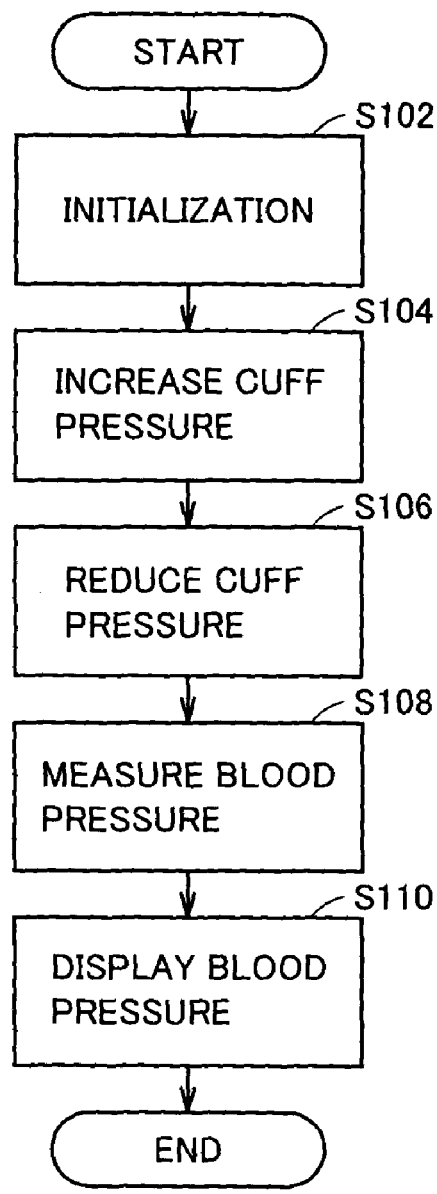
FIG. 4 is a flowchart illustrating the process flow of blood pressure measurement of the blood pressure monitor according to the embodiment of the present invention.

FIG. 4 is a flowchart illustrating the process flow of blood pressure measurement by the blood pressure monitor according to the present embodiment. The program according to this flowchart is prestored in memory portion 114, and the blood pressure measuring process is carried out as CPU 113 reads out this program from memory portion 114 and executes the same.

As shown in FIG. 4, when a subject manipulates a manipulation button on manipulation portion 112 to turn the power ON, blood pressure monitor 100 is initialized (step S102). When it becomes a measurable state, CPU 113 starts driving of pump 123 to gradually increase the cuff pressure of air bag 150 (step S104). During the process of gradually increasing the pressure, when the cuff pressure reaches a prescribed level for measuring the blood pressure, CPU 113 stops pump 123, and gradually opens the closed valve 124 to evacuate the air from air bag 150, so as to gradually reduce the cuff pressure (step S106). In the present embodiment, the blood pressure is measured during the process of gradually decreasing the cuff pressure.

Next, CPU 113 calculates the blood pressure (systolic blood pressure, diastolic blood pressure) in a known manner (step S108). Specifically, during the process where the cuff pressure is gradually decreased, CPU 113 extracts pulse wave information based on the oscillation frequency obtained from oscillation circuit 125. It then calculates the blood pressure value from the pulse wave information extracted. The blood pressure value obtained in step S108 is displayed on display portion 111 (step S110). Although the measurement method described above is based on a so-called "decreasing-pressure measurement method" where the pulse waves are detected while the air bag is being decreased in pressure, it is of course possible to employ a so-called "increasing-pressure measurement method" where the pulse waves are detected while the air bag is being increased in pressure.

Blood pressure monitor 100 and cuff 130 for a blood pressure monitor according to the present embodiment are characterized by a shape of air bag 150 described above. Hereinafter, the shape of air bag 150 will be described in detail for respective examples with reference to the drawings.

Example 1

Figure 5A:
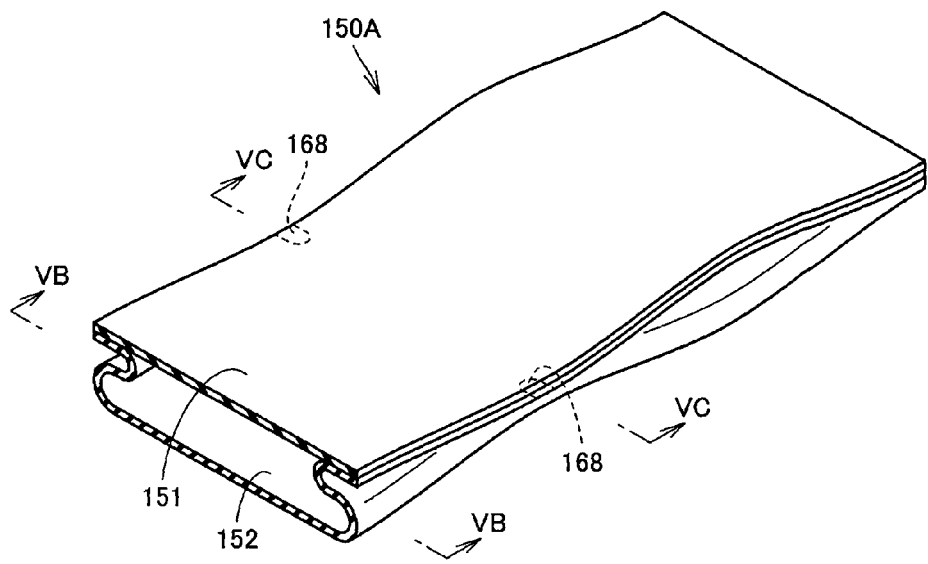
FIG. 5A is a schematic perspective view of an air bag contained in a cuff for a blood pressure monitor according to Example 1 based on the present embodiment, with a part of the air bag being cut out.
Figure 5B:
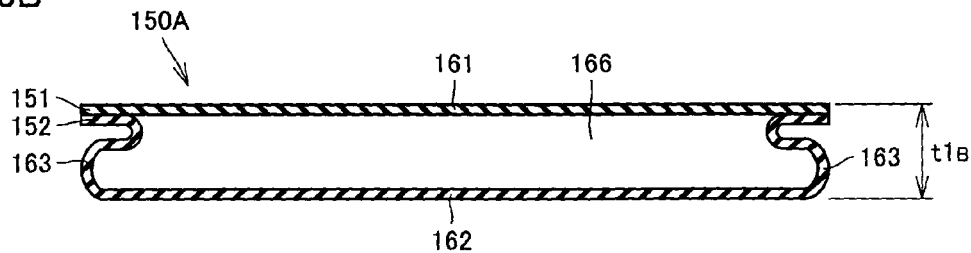
FIG. 5B is a schematic cross sectional view taken along the line VB-VB in FIG. 5A.
Figure 5C:
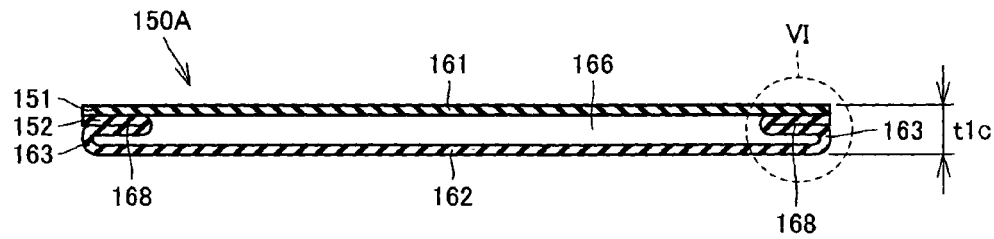
FIG. 5C is a schematic cross sectional view taken along the line VC-VC in FIG. 5A.
Figure 6:
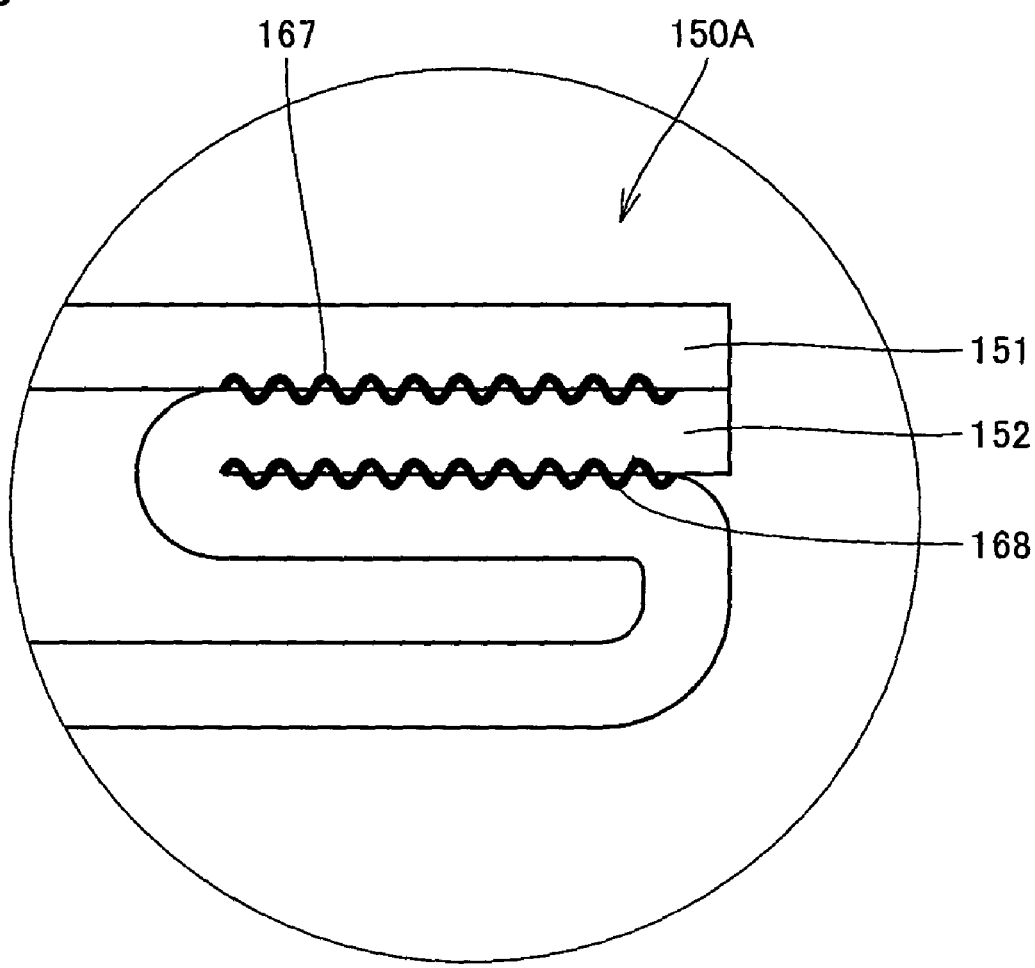
FIG. 6 is an enlarged view of a region VI shown in FIG. 5C.

FIG. 5A is a schematic perspective view of an air bag contained in a cuff for a blood pressure monitor according to Example 1 based on the present embodiment, with a part of the air bag being cut out. FIG. 5B is a schematic cross sectional view taken along the line VB-VB in FIG. 5A, and FIG. 5C is a schematic cross sectional view taken along the line VC-VC in FIG. 5A. FIG. 6 is an enlarged view of a region VI shown in FIG. 5C.

As shown in FIGS. 5A-5C, the air bag 150A of the cuff for a blood pressure monitor of the present example is formed into a bag shape using two resin sheets 151, 152. More specifically, resin sheet 151 of an approximately rectangular shape in two dimensions and resin sheet 152 of an approximately rectangular shape in two dimensions and slightly wider than resin sheet 151 are laid one on the other and their rims are melted and bonded to form air bag 150A having an inflated/deflated space 166 therein.

Resin sheet 152 constitutes an inner wall portion 162 located on an inner side in the state where cuff 130 for a blood pressure monitor is mounted on the wrist. Resin sheet 151 constitutes an outer wall portion 161 located on an outer side than inner wall portion 162 in the state where cuff 130 is mounted on the wrist.

Resin sheet 152 constituting inner wall portion 162 of air bag 150A has its respective end portions folded and melted and bonded to resin sheet 151 constituting outer wall portion 161, to thereby form gussets at side wall portions 163 of air bag 150A. The gussets formed by side wall portions 163 are configured such that they are folded to the inner side of air bag 150A when air bag 150A is in the deflated state. When air bag 150A is inflated, the gussets having been folded in the deflated state come to expand in the thickness direction of air bag 150A. With the function of the gussets, air bag 150A expands sufficiently at and around the side end portions in the width direction of air bag 150A. As such, the artery is adequately pressed for avascularization even at and around the side end portions in the width direction of air bag 150A, whereby high avascularization performance is obtained even if the cuff is narrowed in width.

As shown in FIGS. 5A-5C, in air bag 150A of the cuff for a blood pressure monitor of the present example, a bonded portion 168, identified as a joined portion for reducing expansion of the gusset formed by side wall portion 163, is provided at a region of air bag 150A in its winding direction around the living body (i.e., the longitudinal direction of air bag 150A). A pair of bonded portions 168 are provided at the respective side end portions in the width direction of air bag 150A.

As shown in FIG. 6, bonded portion 168 is distinguished from a bonded portion 167 for sealing air bag 150A in an airtight manner. In air bag 150A of the cuff for a blood pressure monitor of the present example, bonded portion 168 is formed by melting and bonding wall surfaces of side wall portion 163 that would face each other in the state where side wall portion 163 forming the gusset is folded.

With this configuration, in the state where air bag 150A as a single body is inflated, as shown in FIGS. 5B and 5C, the thickness in the longitudinal direction of air bag 150A becomes uneven, with the region provided with bonded portion 168 having a thickness smaller than that of the other region when inflated. That is, the thickness $t1_C$ of the region provided with bonded portion 168 when inflated is smaller than the thickness $t1_B$ of the region not provided with bonded portion 168 when inflated.

In this manner, by forming bonded portion 168 for reducing expansion of the gusset formed by side wall portion 163 in a certain region in the longitudinal direction of air bag 150A, a change in shape of air bag 150A at the side end portion is restricted by the presence of bonded portion 168, which prevents lateral displacement of air bag 150A. On the other hand, in the region not provided with bonded portion 168, the gusset formed by side wall portion 163 promotes expansion of air bag 150A at and around the side end portion in the width direction. This ensures sufficient pressing of the artery for avascularization.

Accordingly, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width.

In air bag 150A of the cuff for a blood pressure monitor of the present example, bonded portion 168 for reducing expansion of the gusset formed by side wall portion 163 is preferably arranged approximately at a central portion in the winding direction of air bag 150A around the living body. With this configuration, it is possible to restrict expansion of the side end portion of air bag 150A approximately at the central portion in the winding direction of air bag 150A around the living body where air bag 150A would expand to the greatest extent in the absence of bonded portion 168. This can effectively prevent occurrence of lateral displacement.

Generally, a wrist blood pressure monitor is configured such that an approximately central portion in the longitudinal direction of the air bag is positioned on the palm side of the wrist in the state where the cuff is wound around the wrist. Under the skin of the palm side of the wrist, a tendon relatively harder than those in the other potions of the wrist is located. Thus, when bonded portion 168 for reducing expansion of the gusset formed by side wall portion 163 is provided approximately at the central portion in the longitudinal direction of air bag 150 as described above, the influence of bonded portion 168 on pressing and avascularization of the artery can be reduced compared to the case of providing bonded portion 168 at another site. As such, it is possible to minimize the adverse effect of degradation in performance of pressing and avascularization attributable to provision of bonded portion 168.

Example 2

Figure 7A:
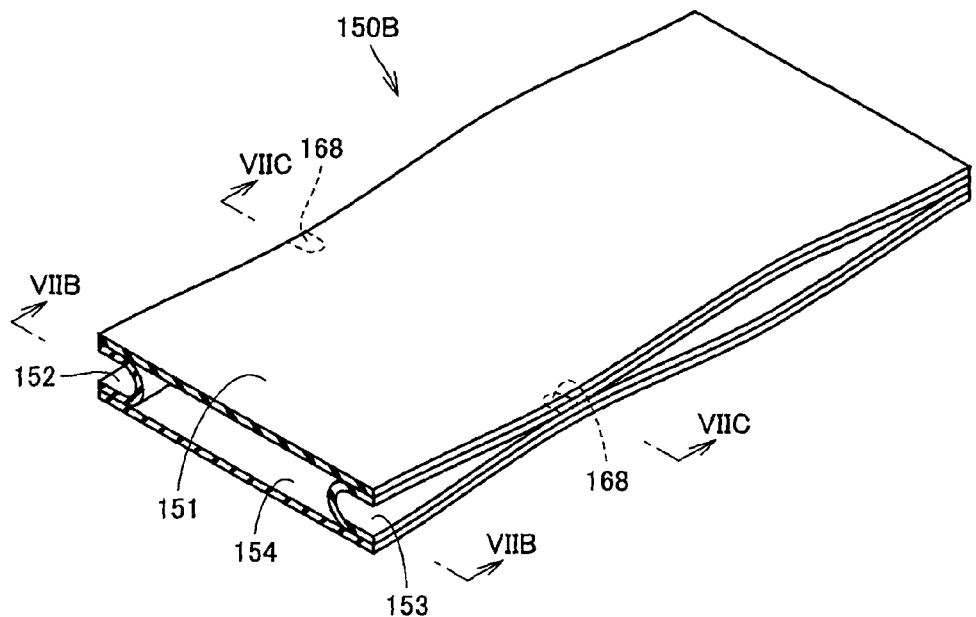
FIG. 7A is a schematic perspective view of an air bag contained in a cuff for a blood pressure monitor according to Example 2 based on the present embodiment, with a part of the air bag being cut out.
Figure 7B:
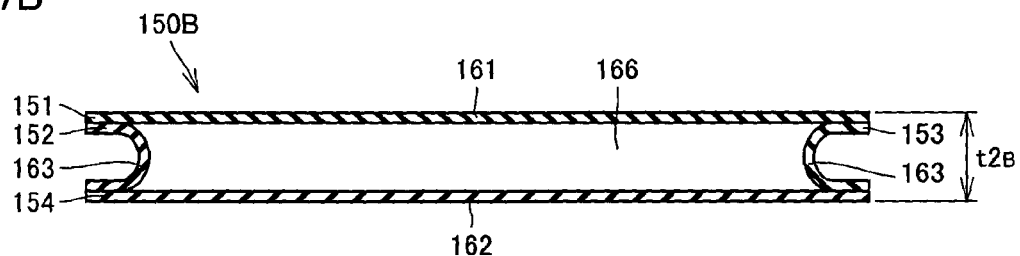
FIG. 7B is a schematic cross sectional view taken along the line VIIB-VIIB in FIG. 7A.
Figure 7C:
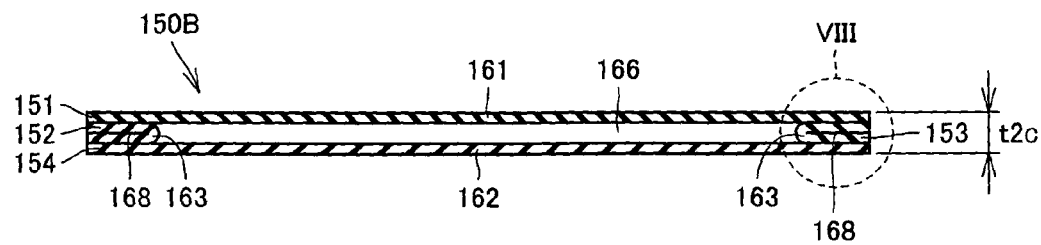
FIG. 7C is a schematic cross sectional view taken along the line VIIC-VIIC in FIG. 7A.
Figure 8:
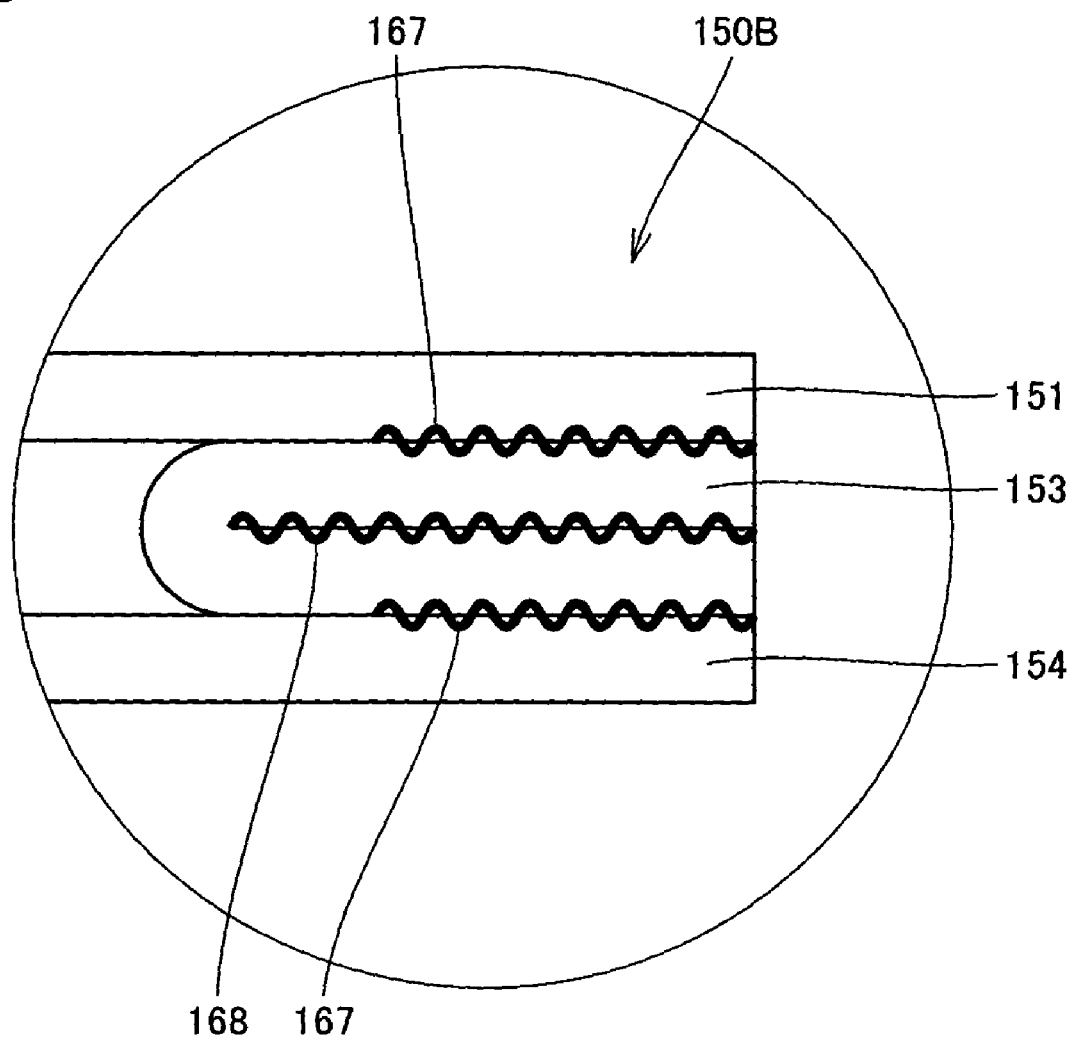
FIG. 8 is an enlarged view of a region VIII shown in FIG. 7C.

FIG. 7A is a schematic perspective view of an air bag contained in a cuff for a blood pressure monitor according to Example 2 based on the present embodiment, with a part of the air bag being cut out. FIG. 7B is a schematic cross sectional view taken along the line VIIB-VIIB in FIG. 7A, and FIG. 7C is a schematic cross sectional view taken along the line VIIC-VIIC in FIG. 7A. FIG. 8 is an enlarged view of a region VIII shown in FIG. 7C.

As shown in FIGS. 7A-7C, the air bag 150B of the cuff for a blood pressure monitor of the present example is formed into a bag shape using four resin sheets 151, 152, 153 and 154. More specifically, two resin sheets 151, 154 of an approximately rectangular shape in two dimensions are laid one on the other, and the side end portions of these two resin sheets 151, 154 are connected using resin sheets 152, 153 of an approximately rectangular shape in two dimensions and narrow in width, respectively, to form air bag 150B. Resin sheets 151, 152, 153 and 154 are connected together, with their rims melted and bonded to the neighboring resin sheets.

Resin sheet 154 constitutes an inner wall portion 162 located on an inner side in the state where cuff 130 for a blood pressure monitor is mounted on the wrist. Resin sheet 151 constitutes an outer wall portion 161 located on an outer side than inner wall portion 162 in the state where cuff 130 is mounted on the wrist.

Further, resin sheets 152, 153 constitute side wall portions 163 connecting inner wall portion 162 and outer wall portion 161. Resin sheets 152, 153 constituting side wall portions 163 of air bag 150B function as the gussets, as in the case of the side wall portions of air bag 150A of the cuff for a blood pressure monitor of Example 1.

As shown in FIGS. 7A-7C, in air bag 150B of the cuff for a blood pressure monitor of the present example, a bonded portion 168, identified as a joined portion for reducing expansion of the gusset formed by side wall portion 163, is provided at a region of air bag 150B in its winding direction around the living body (i.e., the longitudinal direction of air bag 150B). A pair of bonded portions 168 are provided at the respective side end portions in the width direction of air bag 150B.

As shown in FIG. 8, bonded portion 168 is distinguished from a bonded portion 167 for sealing air bag 150B in an airtight manner. In air bag 150B of the cuff for a blood pressure monitor of the present example, bonded portion 168 is formed by melting and bonding wall surfaces of side wall portion 163 that would face each other in the state where side wall portion 163 forming the gusset is folded.

With this configuration, in the state where air bag 150B as a single body is inflated, as shown in FIGS. 7B and 7C, the thickness in the longitudinal direction of air bag 150B becomes uneven, with the region provided with bonded portion 168 having a thickness smaller than that of the other region when inflated. That is, the thickness $t2_C$ of the region provided with bonded portion 168 when inflated is smaller than the thickness $t2_B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width.

In air bag 150B of the cuff for a blood pressure monitor of the present example as well, bonded portion 168 for reducing expansion of the gusset formed by side wall portion 163 is preferably arranged approximately at a central portion in the winding direction of air bag 150B around the living body, for the same reasons as in the case of air bag 150A of the cuff for a blood pressure monitor of Example 1 described above.

Example 3

Figure 9A:
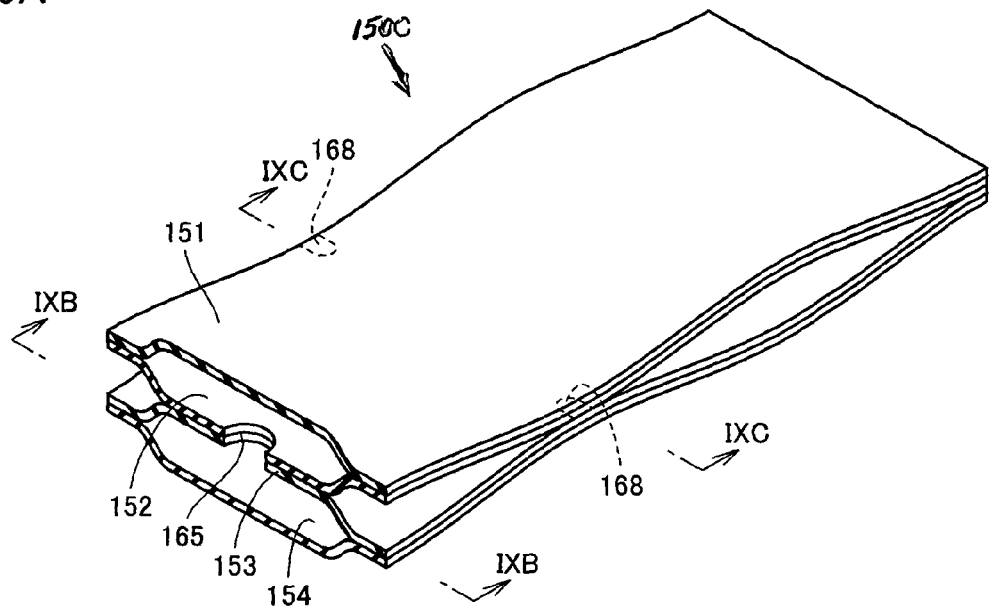
FIG. 9A is a schematic perspective view of an air bag contained in a cuff for a blood pressure monitor according to Example 3 based on the present embodiment, with a part of the air bag being cut out.
Figure 9B:
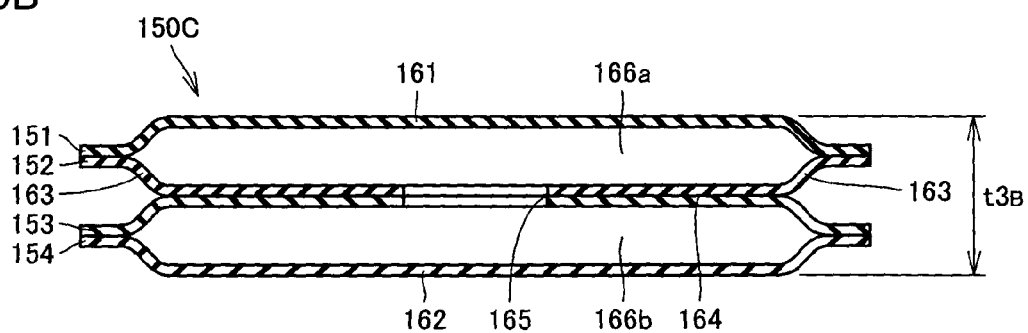
FIG. 9B is a schematic cross sectional view taken along the line IXB-IXB in FIG. 9A.
Figure 9C:
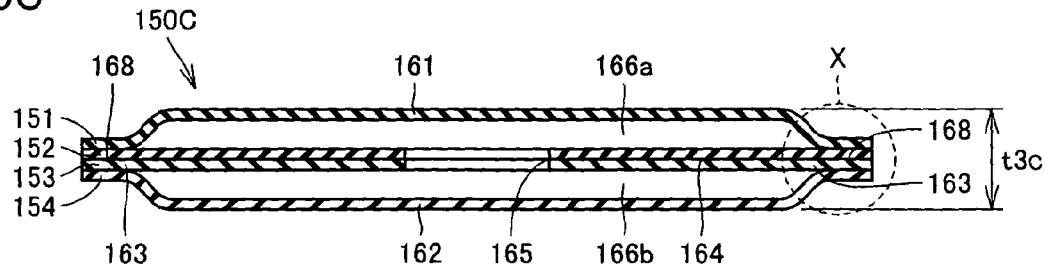
FIG. 9C is a schematic cross sectional view taken along the line IXC-IXC in FIG. 9A.
Figure 10:
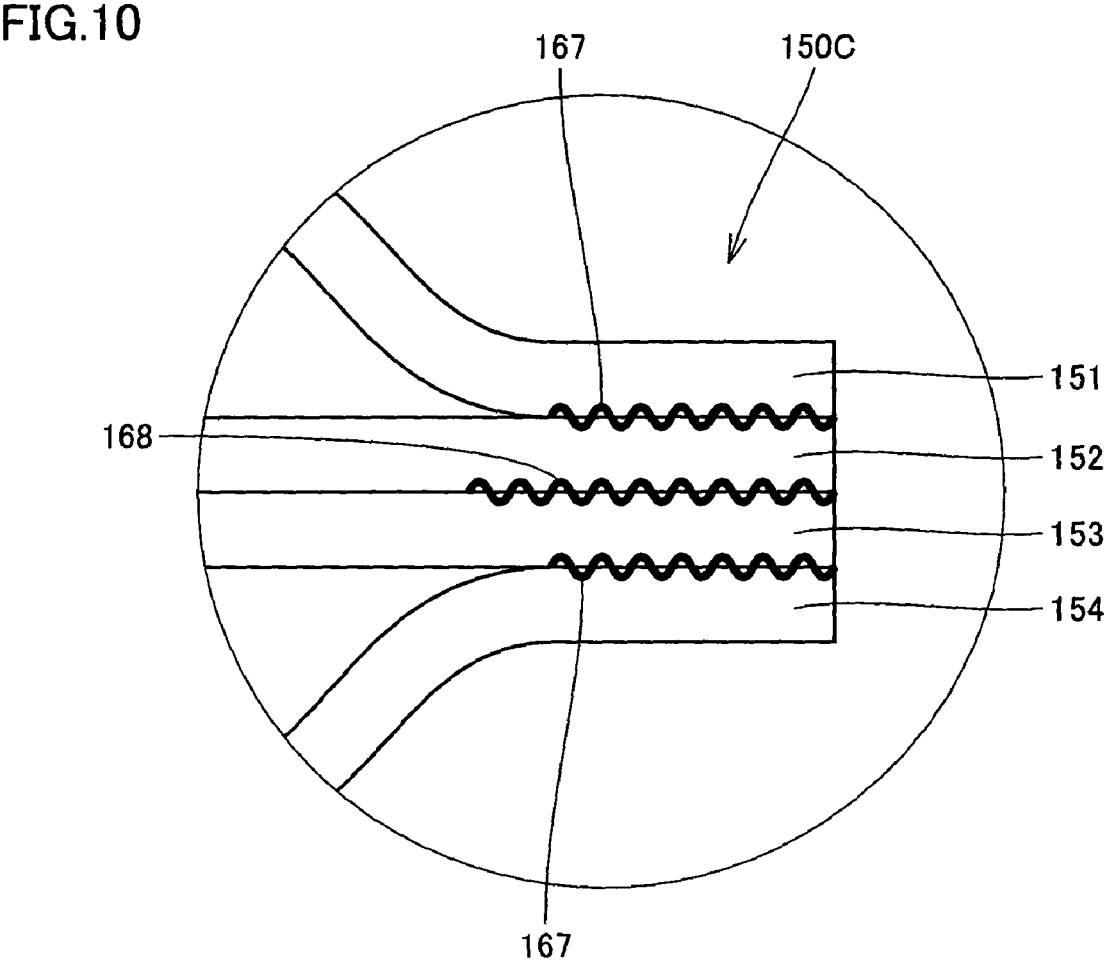
FIG. 10 is an enlarged view of a region X shown in FIG. 9C.

FIG. 9A is a schematic perspective view of an air bag contained in a cuff for a blood pressure monitor according to Example 3 based on the present embodiment, with a part of the air bag being cut out. FIG. 9B is a schematic cross sectional view taken along the line IXB-IXB in FIG. 9A, and FIG. 9C is a schematic cross sectional view taken along the line IXC-IXC in FIG. 9A. FIG. 10 is an enlarged view of a region X shown in FIG. 9C.

As shown in FIGS. 9A-9C, the air bag 150C of the cuff for a blood pressure monitor of the present example is formed into a bag shape using four resin sheets 151, 152, 153 and 154. More specifically, two resin sheets 151, 152 of an approximately rectangular shape in two dimensions are laid one on the other and their rims are melted and bonded to form a first bag member having a first inflated/deflated space 166a therein, two resin sheets 153, 154 of an approximately rectangular shape in two dimensions are laid one on the other and their rims are melted and bonded to form a second bag member having a second inflated/deflated space 166b therein, and the first and second bag members are laid one on the other and melted and bonded at prescribed sites to thereby form an integrated bag member of two layers having first inflated/deflated space 166a and second inflated/deflated space 166b therein. Of the four resin sheets, two resin sheets 152, 153 located in the region where the first and second bag members are connected have holes bored in advance at prescribed positions corresponding to each other, which constitute a communication hole 165 through which first inflated/deflated space 166a and second inflated/deflated space 166b communicate with each other after formation of air bag 150C.

Resin sheet 154 constitutes an inner wall portion 162 located on an inner side in the state where cuff 130 for a blood pressure monitor is mounted on the wrist. Resin sheet 151 constitutes an outer wall portion 161 located on an outer side than inner wall portion 162 in the state where cuff 130 is mounted on the wrist. Further, the respective side end portions in the width direction of resin sheets 152, 153 constitute side wall portions 163 for connecting inner wall portion 162 and outer wall portion 161. The side end portions of resin sheets 152, 153 constituting side wall portions 163 of air bag 150C function as the gussets, as in the case of the side wall portions of air bag 150A of the cuff for a blood pressure monitor of Example 1.

Further, resin sheets 152, 153 constitute a connecting portion 164 located between outer wall portion 161 and inner wall portion 162 inside air bag 150C and connecting a pair of side wall portions 163 located at the respective side end portions of air bag 150C. Connecting portion 164 is for guiding side wall portions 163 serving as the gussets to be surely folded inwards when air bag 150C changes from the inflated state to the deflated state.

As shown in FIGS. 9A-9C, in air bag 150C of the cuff for a blood pressure monitor of the present example, a bonded portion 168, identified as a joined portion for reducing expansion of the gusset formed by side wall portion 163, is provided at a region of air bag 150C in its winding direction around the living body (i.e., the longitudinal direction of air bag 150C). A pair of bonded portions 168 are provided at the respective side end portions in the width direction of air bag 150C.

As shown in FIG. 10, bonded portion 168 is distinguished from a bonded portion 167 for sealing air bag 150C in an airtight manner. In air bag 150C of the cuff for a blood pressure monitor of the present example, bonded portion 168 is formed by melting and bonding wall surfaces of side wall portion 163 that would face each other in the state where side wall portion 163 forming the gusset is folded.

With this configuration, in the state where air bag 150C as a single body is inflated, as shown in FIGS. 9B and 9C, the thickness in the longitudinal direction of air bag 150C becomes uneven, with the region provided with bonded portion 168 having a thickness smaller than that of the other region when inflated. That is, the thickness $t3_C$ of the region provided with bonded portion 168 when inflated is smaller than the thickness $t3^B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width.

In air bag 150C of the cuff for a blood pressure monitor of the present example as well, bonded portion 168 for reducing expansion of the gusset formed by side wall portion 163 is preferably arranged approximately at a central portion in the winding direction of air bag 150C around the living body, for the same reasons as in the case of air bag 150A of the cuff for a blood pressure monitor of Example 1 described above.

Example 4

Figure 11A:
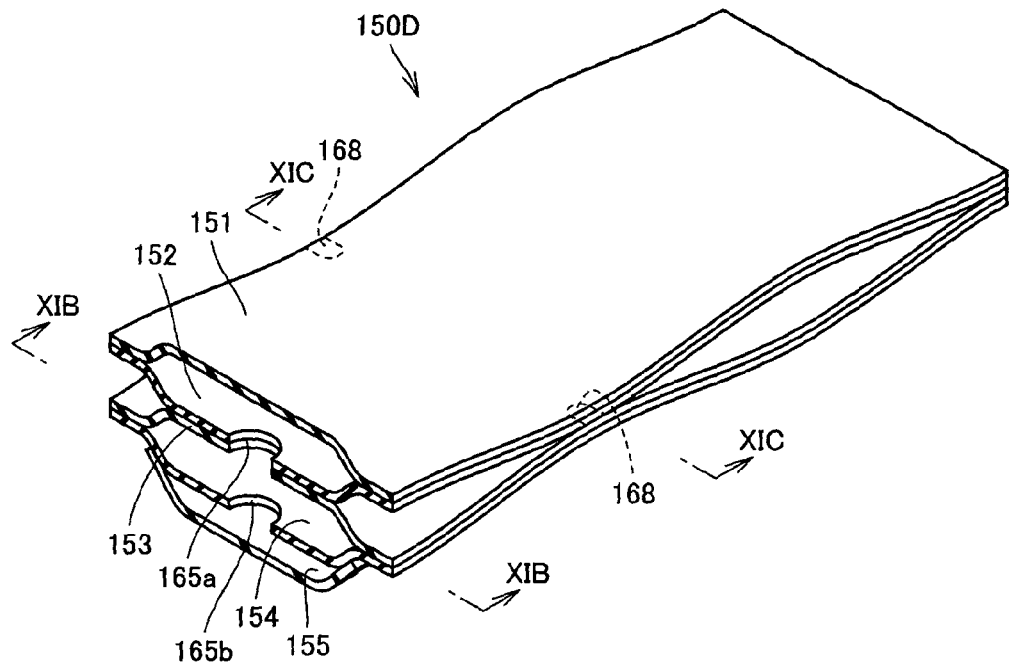
FIG. 11A is a schematic perspective view of an air bag contained in a cuff for a blood pressure monitor according to Example 4 based on the present embodiment, with a part of the air bag being cut out.
Figure 11B:
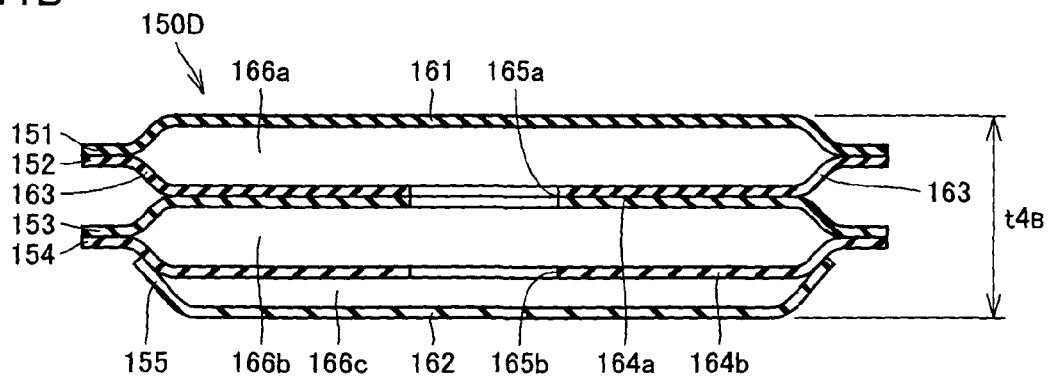
FIG. 11B is a schematic cross sectional view taken along the line XIB-XIB in FIG. 11A.
Figure 11C:
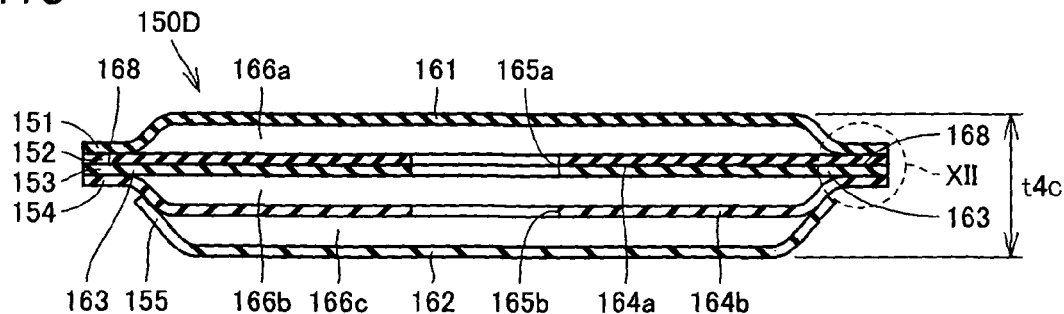
FIG. 11C is a schematic cross sectional view taken along the line XIC-XIC in FIG. 11A.
Figure 12:
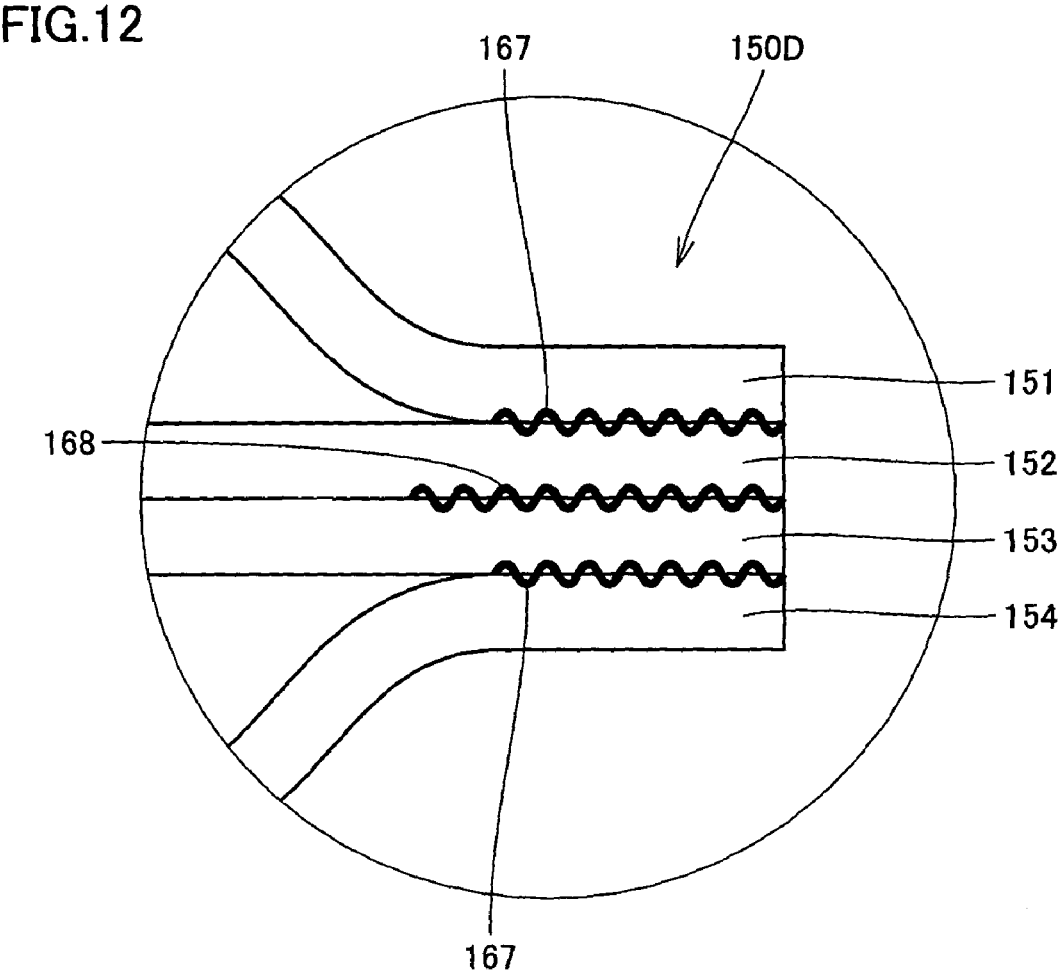
FIG. 12 is an enlarged view of a region XII shown in FIG. 11C.

FIG. 11A is a schematic perspective view of an air bag contained in a cuff for a blood pressure monitor according to Example 4 based on the present embodiment, with a part of the air bag being cut out. FIG. 11B is a schematic cross sectional view taken along the line XIB-XIB in FIG. 11A, and FIG. 11C is a schematic cross sectional view taken along the line XIC-XIC in FIG. 11A. FIG. 12 is an enlarged view of a region XII shown in FIG. 11C.

As shown in FIGS. 11A-11C, the air bag 150D of the cuff for a blood pressure monitor of the present example is formed into a bag shape using five resin sheets 151, 152, 153, 154 and 155. More specifically, two resin sheets 151, 152 of an approximately rectangular shape in two dimensions are laid one on the other and their rims are melted and bonded to form a first bag member having a first inflated/deflated space 166a therein, two resin sheets 153, 154 of an approximately rectangular shape in two dimensions are laid one on the other and their rims are melted and bonded to form a second bag member having a second inflated/deflated space 166b therein, and the first and second bag members are laid one on the other and melted and bonded at prescribed sites to thereby form an integrated bag member of two layers having first inflated/deflated space 166a and second inflated/deflated space 166b therein. Further, a resin sheet 155 of an approximately rectangular shape in two dimensions and slightly narrower in width is laid on the above-described integrated bag member, and a rim of resin sheet 155 is melted and bonded to a prescribed position on the outer surface of resin sheet 154 of the integrated bag member, to thereby form an integrated bag member of three layers having a third inflated/deflated space 166c in addition to the above-described first and second inflated/deflated spaces 166a and 166b. Of the five resin sheets, two resin sheets 152, 153 partitioning first and second inflated/deflated spaces 166a and 166b have holes bored in advance at prescribed positions corresponding to each other, which constitute a communication hole 165a through which first inflated/deflated space 166a and second inflated/deflated space 166b communicate with each other after formation of air bag 150D. Furthermore, of the five resin sheets, resin sheet 154 partitioning second and third inflated/deflated spaces 166b and 166c has a hole bored in advance at a prescribed position, which constitutes a communication hole 165b through which second inflated/deflated space 166b and third inflated/deflated space 166c communicate with each other after formation of air bag 150D.

Resin sheet 155 constitutes an inner wall portion 162 located on an inner side in the state where cuff 130 for a blood pressure monitor is mounted on the wrist. Resin sheet 151 constitutes an outer wall portion 161 located on an outer side than inner wall portion 162 in the state where cuff 130 is mounted on the wrist. Further, the respective side end portions in the width direction of resin sheets 152, 153 constitute side wall portions 163 for connecting inner wall portion 162 and outer wall portion 161. The side end portions of resin sheets 152, 153 constituting side wall portions 163 of air bag 150D function as the gussets, as in the case of the side wall portions of air bag 150A of the cuff for a blood pressure monitor of Example 1.

Further, resin sheets 152, 153 constitute a connecting portion 164a located between outer wall portion 161 and inner wall portion 162 inside air bag 150D and connecting a pair of side wall portions 163 located at the respective side end portions of air bag 150D. Furthermore, resin sheet 154 constitutes a connecting portion 164b located between outer wall portion 161 and inner wall portion 162 inside air bag 150D and connecting a pair of side wall portions 163 located at the respective side end portions of air bag 150D. Connecting portions 164a, 164b are for guiding side wall portions 163 serving as the gussets to be surely folded inwards when air bag 150D changes from the inflated state to the deflated state.

As shown in FIGS. 11A-11C, in air bag 150D of the cuff for a blood pressure monitor of the present example, a bonded portion 168, identified as a joined portion for reducing expansion of the gusset formed by side wall portion 163, is provided at a region of air bag 150D in its winding direction around the living body (i.e., the longitudinal direction of air bag 150D). A pair of bonded portions 168 are provided at the respective side end portions in the width direction of air bag 150D.

As shown in FIG. 12, bonded portion 168 is distinguished from a bonded portion 167 for sealing air bag 150D in an airtight manner. In air bag 150D of the cuff for a blood pressure monitor of the present example, bonded portion 168 is formed by melting and bonding wall surfaces of side wall portion 163 that would face each other in the state where side wall portion 163 forming the gusset is folded.

With this configuration, in the state where air bag 150D as a single body is inflated, as shown in FIGS. 11B and 11C, the thickness in the longitudinal direction of air bag 150D becomes uneven, with the region provided with bonded portion 168 having a thickness smaller than that of the other region when inflated. That is, the thickness $t4_C$ of the region provided with bonded portion 168 when inflated is smaller than the thickness $t4_B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width.

In air bag 150D of the cuff for a blood pressure monitor of the present example as well, bonded portion 168 for reducing expansion of the gusset formed by side wall portion 163 is preferably arranged approximately at a central portion in the winding direction of air bag 150D around the living body, for the same reasons as in the case of air bag 150A of the cuff for a blood pressure monitor of Example 1 described above.

Example 5

Figure 13A:
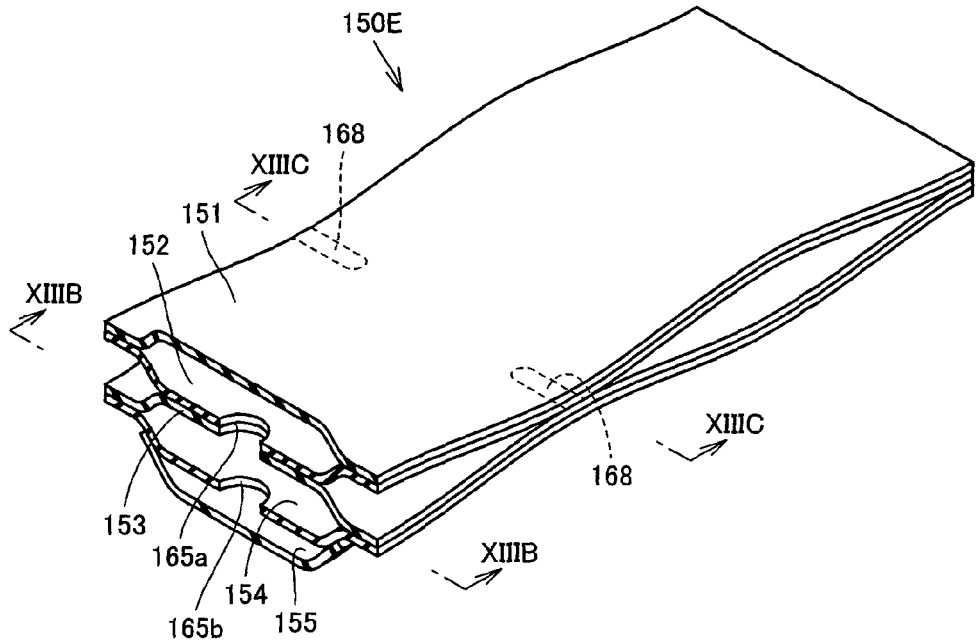
FIG. 13A is a schematic perspective view of an air bag contained in a cuff for a blood pressure monitor according to Example 5 based on the present embodiment, with a part of the air bag being cut out.
Figure 13B:
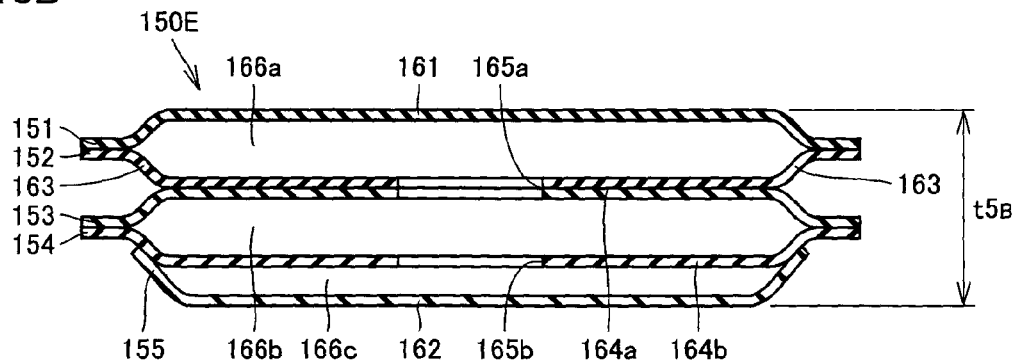
FIG. 13B is a schematic cross sectional view taken along the line XIIIB-XIIIB in FIG. 13A.
Figure 13C:
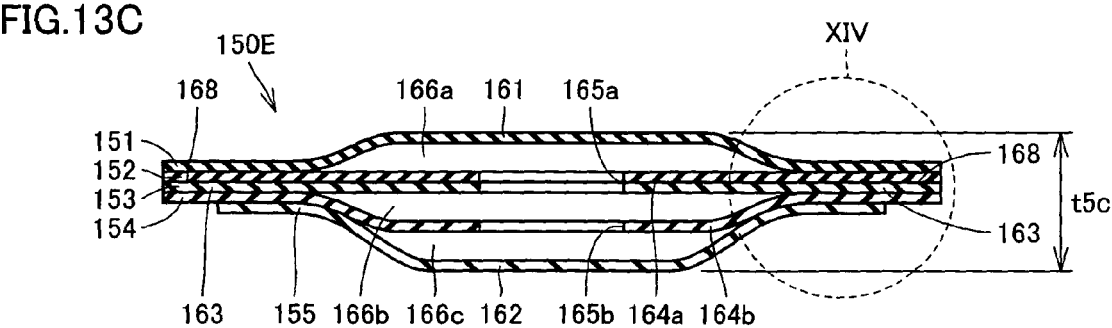
FIG. 13C is a schematic cross sectional view taken along the line XIIIC-XIIIC in FIG. 13A.
Figure 14:
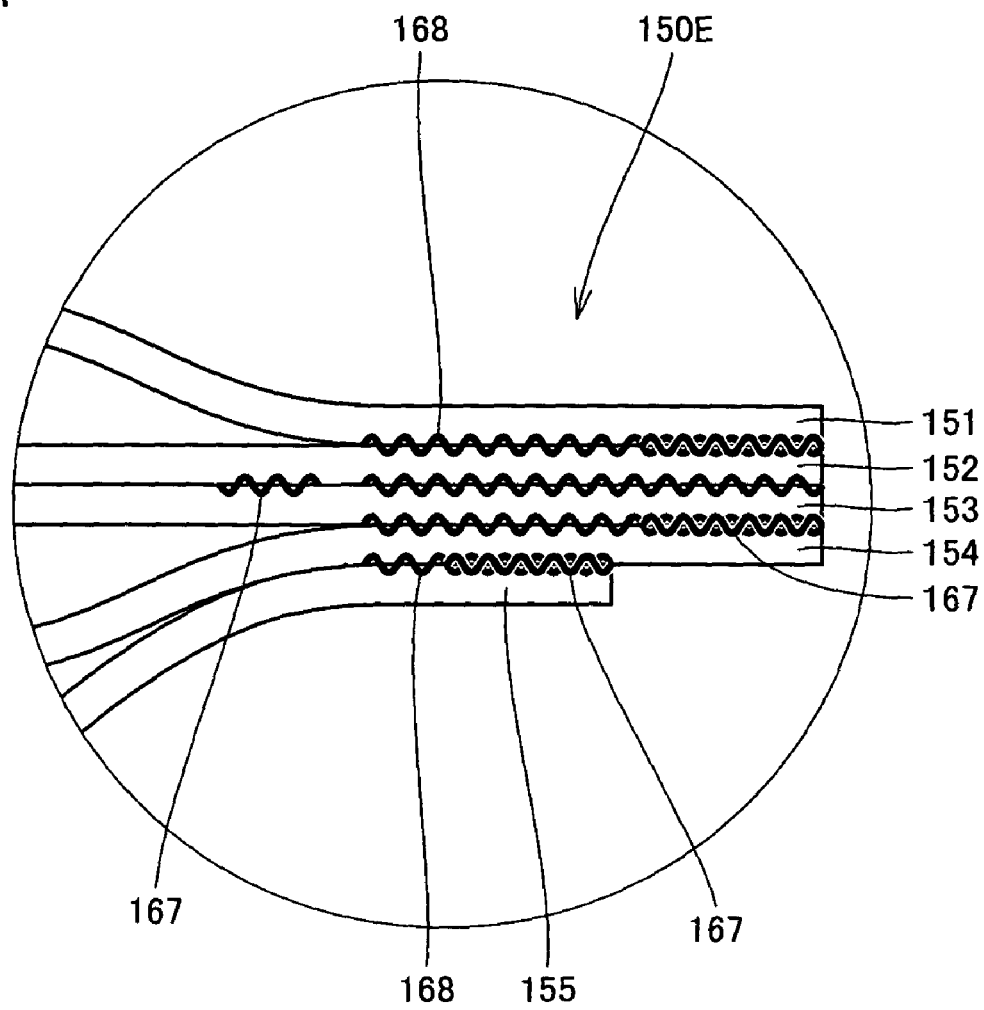
FIG. 14 is an enlarged view of a region XIV shown in FIG. 13C.

FIG. 13A is a schematic perspective view of an air bag contained in a cuff for a blood pressure monitor according to Example 5 based on the present embodiment, with a part of the air bag being cut out. FIG. 13B is a schematic cross sectional view taken along the line XIIIB-XIIIB in FIG. 13A, and FIG. 13C is a schematic cross sectional view taken along the line XIIIC-XIIIC in FIG. 13A. FIG. 14 is an enlarged view of a region XIV shown in FIG. 13C. The portions identical to those of air bag 150D of the cuff for a blood pressure monitor of Example 4 have the same reference characters allotted, and description thereof will not be repeated.

As shown in FIGS. 13A-13C, the air bag 150E of the cuff for a blood pressure monitor of the present example is formed into a bag shape using five resin sheets 151, 152, 153, 154 and 155, as in the case of air bag 150D of the cuff for a blood pressure monitor of Example 4 described above. Further, in air bag 150E of the cuff for a blood pressure monitor of the present example, a bonded portion 168, identified as a joined portion for reducing expansion of the gusset formed by side wall portion 163, is provided at a region of air bag 150E in its winding direction around the living body (i.e., the longitudinal direction of air bag 150E). A pair of bonded portions 168 are provided at the respective side end portions in the width direction of air bag 150E, which extend further inwards of air bag 150E compared to bonded portions 168 provided at the side end portions of air bag 150D of the cuff for a blood pressure monitor of Example 4.

As shown in FIG. 14, bonded portion 168 is distinguished from a bonded portion 167 for sealing air bag 150E in an airtight manner. In air bag 150E of the cuff for a blood pressure monitor of the present example, bonded portion 168 is formed in the following manner. The wall surfaces of side wall portion 163 that would face each other in the state where side wall portion 163 forming the gusset is folded are melted and bonded together. Further, the wall surface of inner wall portion 162 and the wall surface of outer wall portion 161 that would face the corresponding wall surfaces of side wall portion 163 when side wall portion 163 is folded are melted and bonded to the relevant wall surfaces of side wall portion 163, to thereby form bonded portion 168. Melting and bonding of the wall surfaces of side wall portion 163, melting and bonding of the wall surface of side wall portion 163 and the wall surface of outer wall portion 161, and melting and bonding of the wall surface of side wall portion 163 and the wall surface of inner wall portion 162 are performed in an integrated manner by a melting and bonding process of one time.

With this configuration, in the state where air bag 150E as a single body is inflated, as shown in FIGS. 13B and 13C, the thickness in the longitudinal direction of air bag 150E becomes uneven, with the region provided with bonded portion 168 having a thickness smaller than that of the other region when inflated. That is, the thickness $t5_C$ of the region provided with bonded portion 168 when inflated is smaller than the thickness $t5_B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width. It is noted that bonded portion 168 provided in air bag 150E of the cuff for a blood pressure monitor of the present example extends further inwards in the width direction of the air bag than bonded portion 168 provided in air bag 150D of the cuff for a blood pressure monitor of Example 4. This prevents lateral movement still more reliably.

Furthermore, in air bag 150E of the cuff for a blood pressure monitor of the present example as well, bonded portion 168 for reducing expansion of the gusset formed by side wall portion 163 is preferably arranged approximately at a central portion in the winding direction of air bag 150E around the living body, for the same reasons as in the case of air bag 150A of the cuff for a blood pressure monitor of Example 1 described above.

Example 6

Figure 15A:
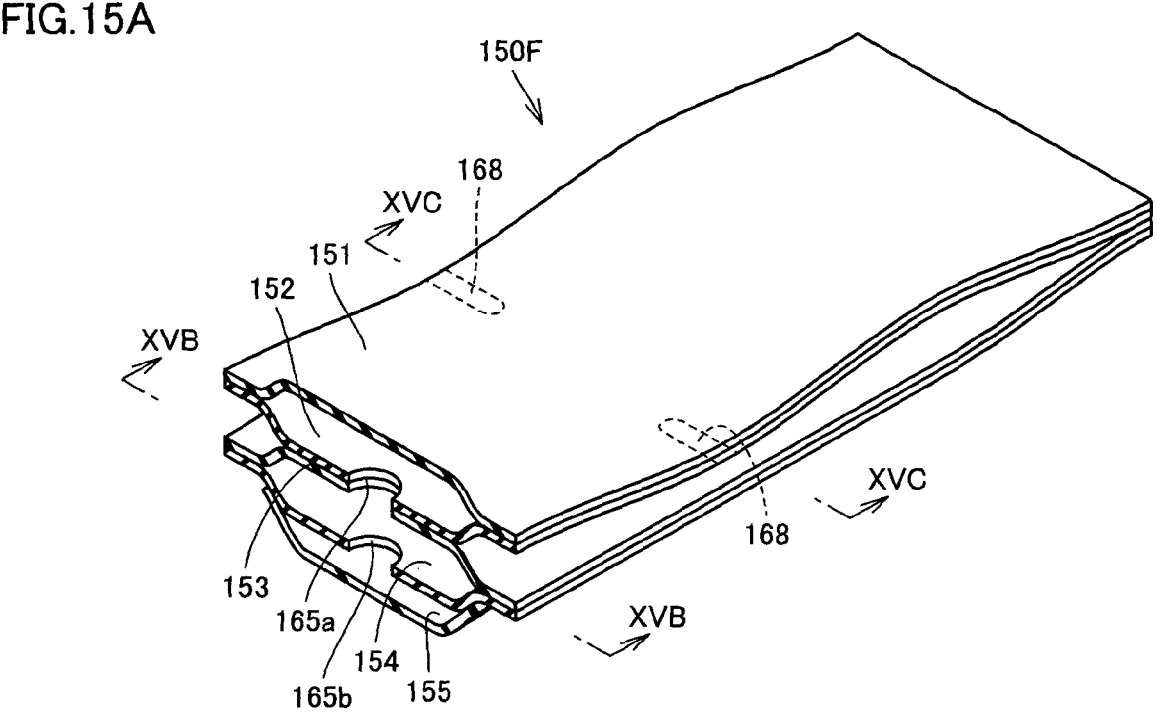
FIG. 15A is a schematic perspective view of an air bag contained in a cuff for a blood pressure monitor according to Example 6 based on the present embodiment, with a part of the air bag being cut out.
Figure 15B:
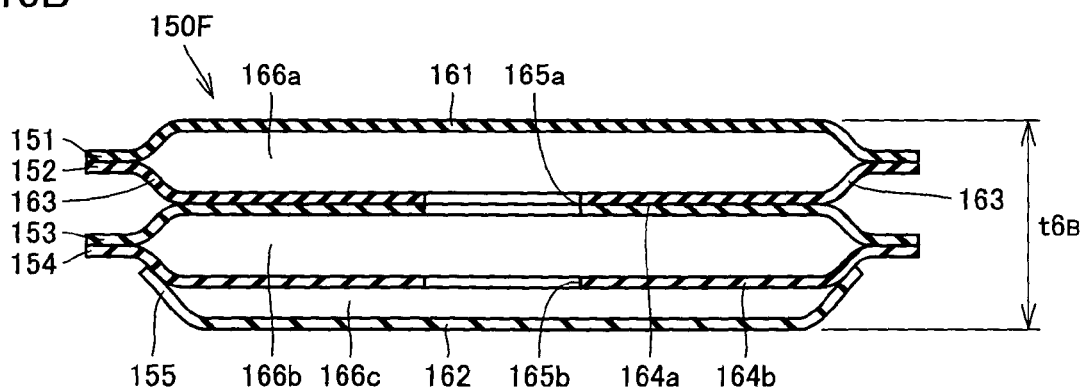
FIG. 15B is a schematic cross sectional view taken along the line XVB-XVB in FIG. 15A.
Figure 15C:
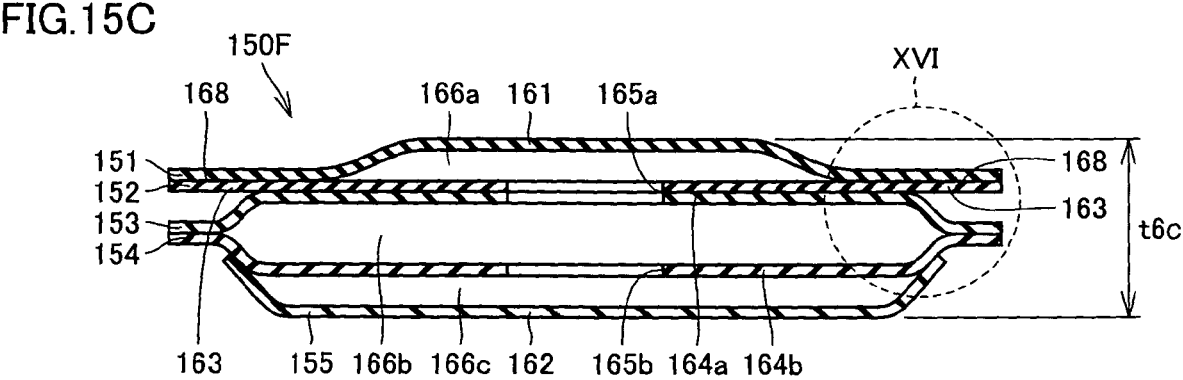
FIG. 15C is a schematic cross sectional view taken along the line XVC-XVC in FIG. 15A.
Figure 16:
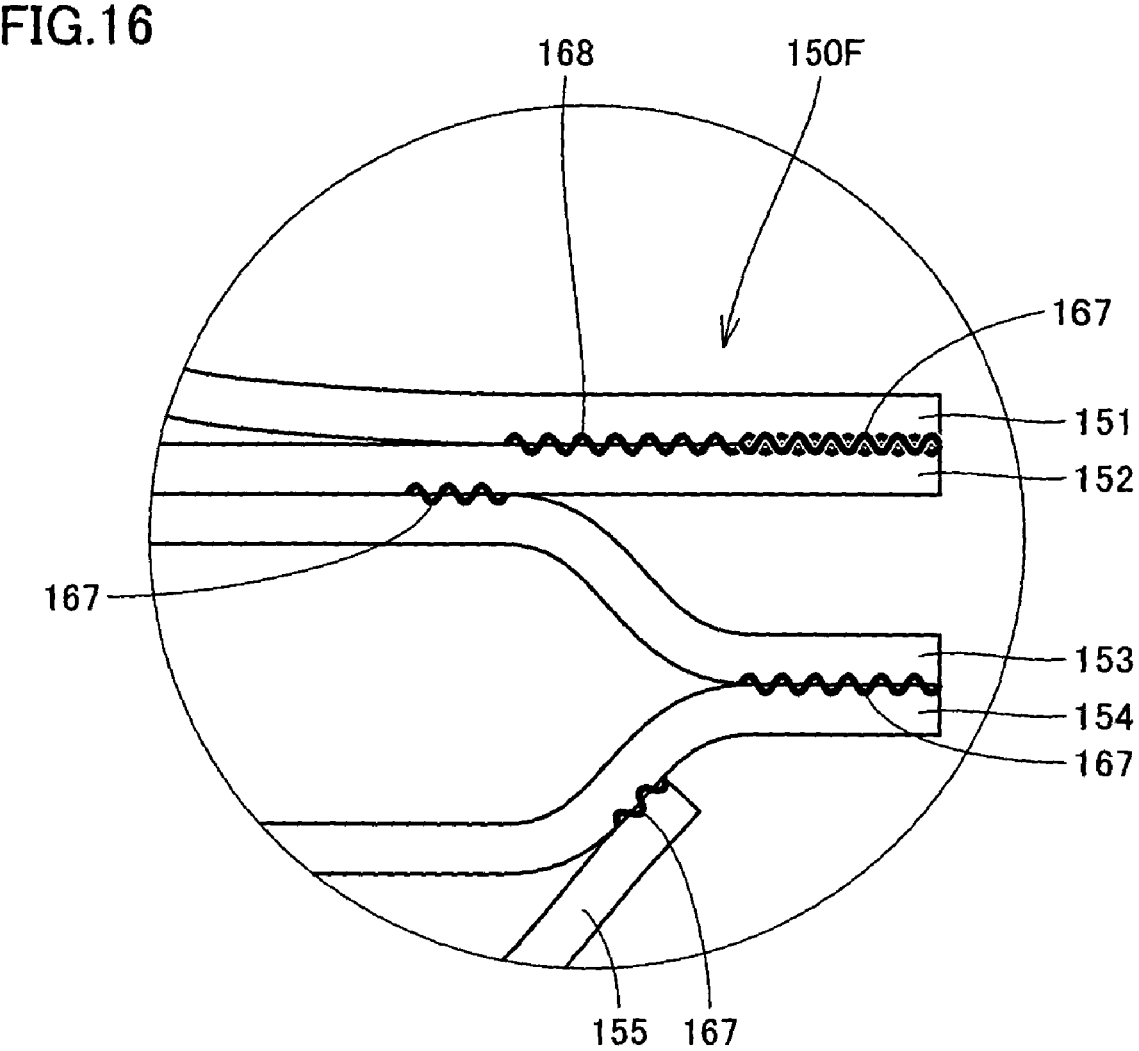
FIG. 16 is an enlarged view of a region XVI shown in FIG. 15C.

FIG. 15A is a schematic perspective view of an air bag contained in a cuff for a blood pressure monitor according to Example 6 based on the present embodiment, with a part of the air bag being cut out. FIG. 15B is a schematic cross sectional view taken along the line XVB-XVB in FIG. 15A, and FIG. 15C is a schematic cross sectional view taken along the line XVC-XVC in FIG. 15A. FIG. 16 is an enlarged view of a region XVI shown in FIG. 15C. The portions identical to those of air bag 150D of the cuff for a blood pressure monitor of Example 4 have the same reference characters allotted, and description thereof will not be repeated.

As shown in FIGS. 15A-15C, the air bag 150F of the cuff for a blood pressure monitor of the present example is formed into a bag shape using five resin sheets 151, 152, 153, 154 and 155, as in the case of air bag 150D of the cuff for a blood pressure monitor of Example 4 described above. Further, in air bag 150F of the cuff for a blood pressure monitor of the present example, a bonded portion 168, identified as a joined portion for reducing expansion of the gusset formed by side wall portion 163, is provided at a region of air bag 150F in its winding direction around the living body (i.e., the longitudinal direction of air bag 150F). A pair of bonded portions 168 are provided at the respective side end portions in the width direction of air bag 150F.

As shown in FIG. 16, bonded portion 168 is distinguished from a bonded portion 167 for sealing air bag 150F in an airtight manner. In air bag 150F of the cuff for a blood pressure monitor of the present example, as shown in FIG. 16, bonded portion 168 is formed in a manner different from the case of air bag 150D of the cuff for a blood pressure monitor of Example 4. Specifically, a wall surface of side wall portion 163 forming the gusset and the wall surface of outer wall portion 161 that the relevant wall surface of side wall portion 163 would face in the state where side wall portion 163 is folded, are melted and bonded to form bonded portion 168. As such, of first through third inflated/deflated spaces 166a, 166b and 166c arranged one-on another inside air bag 150F, expansion of only first inflated/deflated space 166a located outermost is restricted by provision of bonded portion 168.

With this configuration, in the state where air bag 150F as a single body is inflated, as shown in FIGS. 15B and 15C, the thickness in the longitudinal direction of air bag 150F becomes uneven, with the region provided with bonded portion 168 having a thickness smaller than that of the other region when inflated. That is, the thickness $t6_C$ of the region provided with bonded portion 168 when inflated is smaller than the thickness $t6_B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width.

Furthermore, in air bag 150F of the cuff for a blood pressure monitor of the present example, as in the case of air bag 150A of the cuff for a blood pressure monitor of Example 1 described above, bonded portion 168 for reducing expansion of the gusset formed by side wall portion 163 is preferably arranged approximately at a central portion in the winding direction of air bag 150F around the living body. With this configuration, it is possible to effectively suppress occurrence of lateral displacement, and also minimize an adverse effect of degradation of avascularization performance attributable to provision of bonded portion 168.

If the cuff is configured such that a tendon located beneath the skin on the palm side of the wrist is not pressed at all, the artery located by the side of the tendon will be pressed by the air bag and will move to the back of the tendon, inwards of the wrist. If the artery moves to the back of the tendon, the pressing force caused by inflation of the air bag will not sufficiently be exerted on the artery, in which case the avascularization performance will rather be degraded. This means that the portion of the wrist where the tendon is located also needs to be pressed by the air bag to some extent.

In air bag 150F of the cuff for a blood pressure monitor according to the present example, bonded portion 168 restricts expansion of only first inflated/deflated space 166a located outermost among first through third inflated/deflated spaces 166a, 166b, 166c laid one on another in the thickness direction, as described above, and thus, other inflated/deflated spaces 166b and 166c expand sufficiently. Accordingly, air bag 150F can press the portion of the wrist where the tendon is located to some extent when inflated, which avoids deterioration of the avascularization performance as described above.

Example 7

Figure 17A:
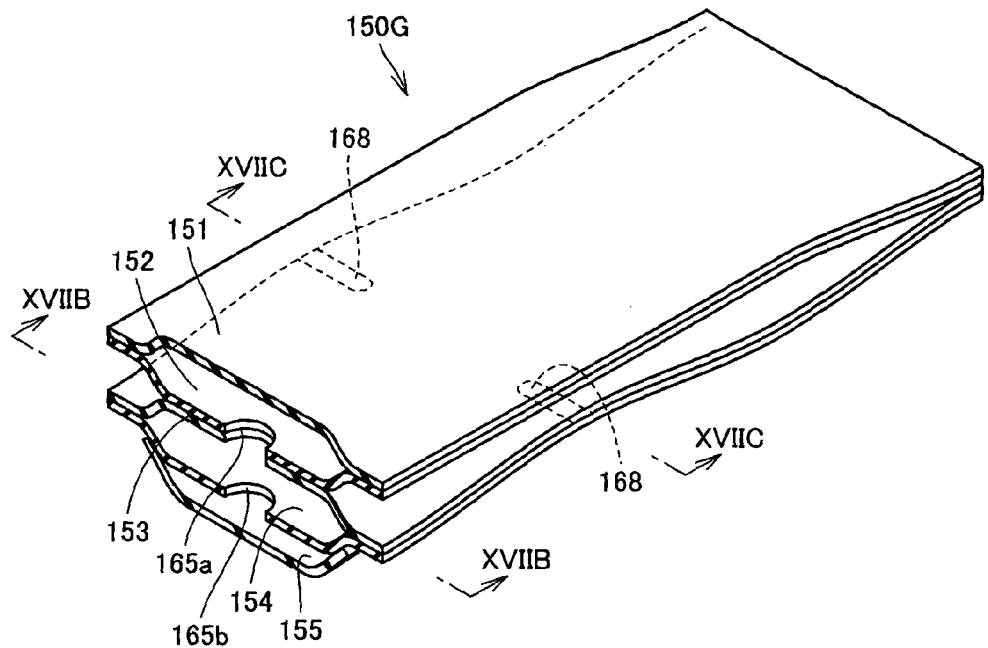
FIG. 17A is a schematic perspective view of an air bag contained in a cuff for a blood pressure monitor according to Example 7 based on the present embodiment, with a part of the air bag being cut out.
Figure 17B:
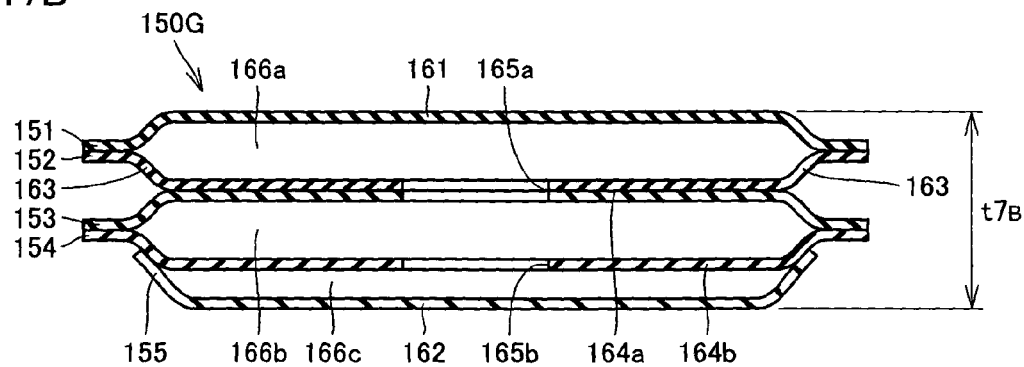
FIG. 17B is a schematic cross sectional view taken along the line XVIIB-XVIIB in FIG. 17A.
Figure 17C:
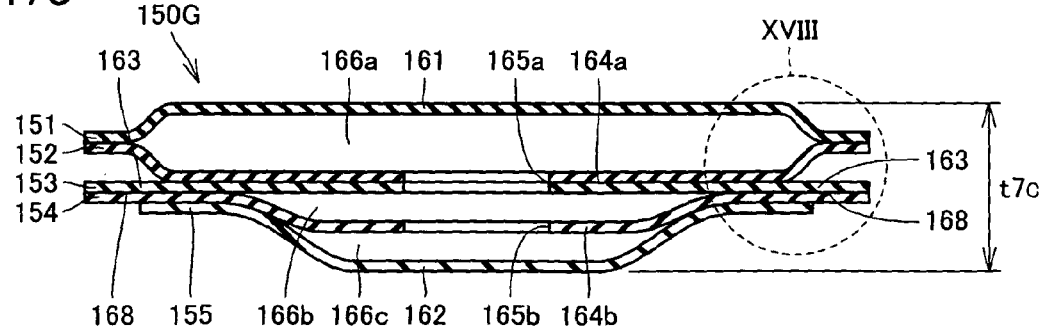
FIG. 17C is a schematic cross sectional view taken along the line XVIIC-XVIIC in FIG. 17A.
Figure 18:
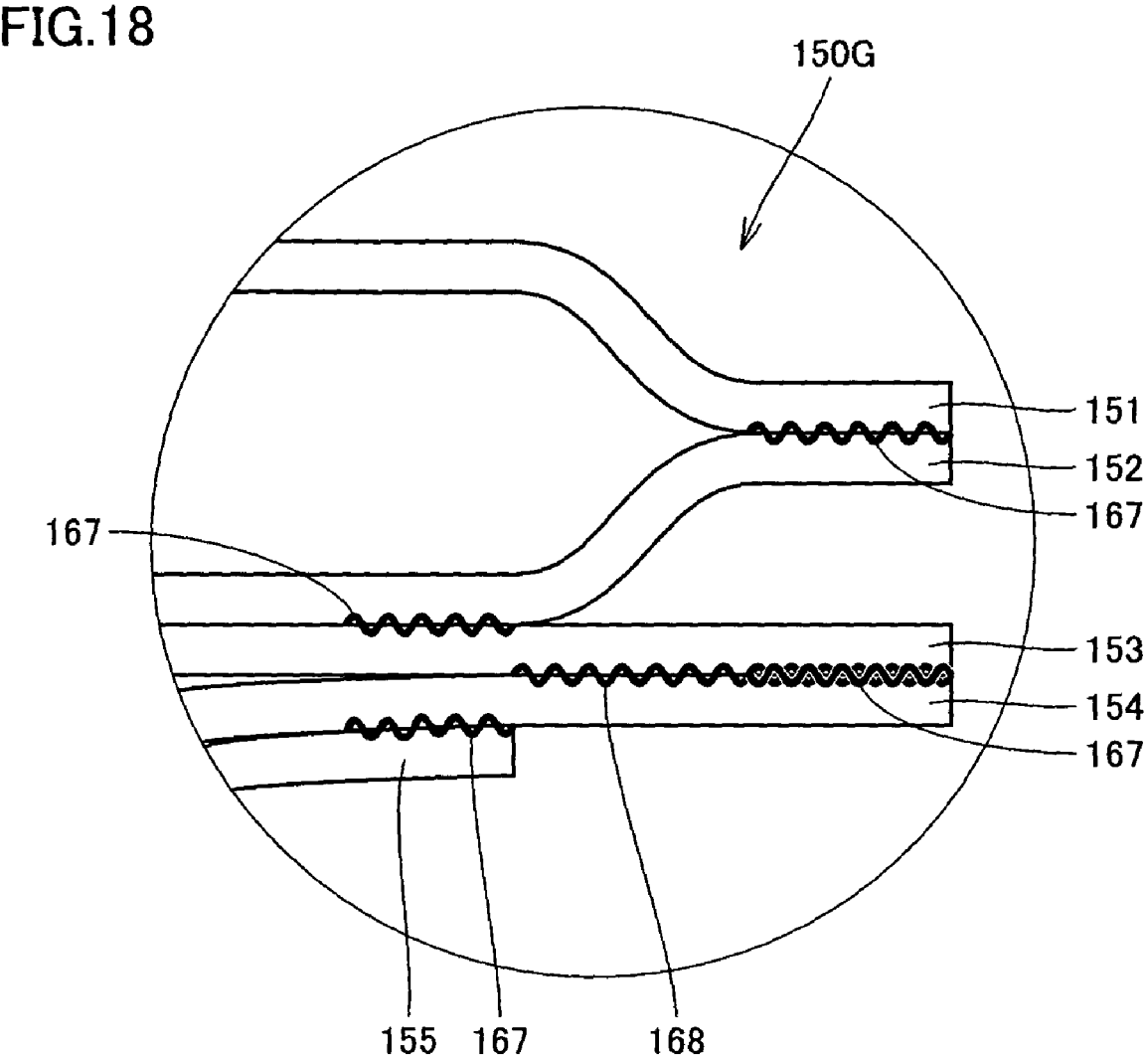
FIG. 18 is an enlarged view of a region XVIII shown in FIG. 17C.

FIG. 17A is a schematic perspective view of an air bag contained in a cuff for a blood pressure monitor according to Example 7 based on the present embodiment, with a part of the air bag being cut out. FIG. 17B is a schematic cross sectional view taken along the line XVIIB-XVIIB in FIG. 17A, and FIG. 17C is a schematic cross sectional view taken along the line XVIIC-XVIIC in FIG. 17A. FIG. 18 is an enlarged view of a region XVIII shown in FIG. 17C. The portions identical to those of air bag 150D of the cuff for a blood pressure monitor of Example 4 have the same reference characters allotted, and description thereof will not be repeated.

As shown in FIGS. 17A-17C, the air bag 150G of the cuff for a blood pressure monitor of the present example is formed into a bag shape using five resin sheets 151, 152, 153, 154 and 155, as in the case of air bag 150D of the cuff for a blood pressure monitor of Example 4 described above. Further, in air bag 150G of the cuff for a blood pressure monitor of the present example, a bonded portion 168, identified as a joined portion for reducing expansion of the gusset formed by side wall portion 163, is provided at a region of air bag 150G in its winding direction around the living body (i.e., the longitudinal direction of air bag 150G). A pair of bonded portions 168 are provided at the respective side end portions in the width direction of air bag 150G.

As shown in FIG. 18, bonded portion 168 is distinguished from a bonded portion 167 for sealing air bag 150G in an airtight manner. In air bag 150G of the cuff for a blood pressure monitor of the present example, as shown in FIG. 18, bonded portion 168 is formed in a manner different from the case of air bag 150D of the cuff for a blood pressure monitor of Example 4. Specifically, a wall surface of side wall portion 163 and the wall surface of inner wall portion 162 that the relevant wall surface of side wall portion 163 would face in the state where side wall portion 163 forming the gusset is folded, are melted and bonded to form bonded portion 168. As such, of first through third inflated/deflated spaces 166a, 166b and 166c arranged one on another inside air bag 150G, expansion of only second inflated/deflated space 166b located in the middle is restricted by provision of bonded portion 168.

With this configuration, in the state where air bag 150G as a single body is inflated, as shown in FIGS. 17B and 17C, the thickness in the longitudinal direction of air bag 150G becomes uneven, with the region provided with bonded portion 168 having a thickness smaller than that of the other region when inflated. That is, the thickness $t7_C$ of the region provided with bonded portion 168 when inflated is smaller than the thickness $t7_B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width.

Furthermore, in air bag 150G of the cuff for a blood pressure monitor of the present example, as in the case of air bag 150A of the cuff for a blood pressure monitor of Example 1 described above, bonded portion 168 for reducing expansion of the gusset formed by side wall portion 163 is preferably arranged approximately at a central portion in the winding direction of air bag 150G around the living body. With this configuration, it is possible to effectively suppress occurrence of lateral displacement, and also minimize an adverse effect of degradation of avascularization performance attributable to provision of bonded portion 168.

Further, in air bag 150G of the cuff for a blood pressure monitor according to the present example, bonded portion 168 restricts expansion of only second inflated/deflated space 166b located in the middle among first through third inflated/deflated spaces 166a, 166b, 166c laid one on another in the thickness direction, as described above, and thus, other inflated/deflated spaces 166a and 166c expand sufficiently. Accordingly, as in the case of air bag 150F of the cuff for a blood pressure monitor of Example 6 described above, air bag 150G can press the portion of the wrist where the tendon is located to some extent when inflated, which avoids deterioration of the avascularization performance.

Example 8

Figure 19A:
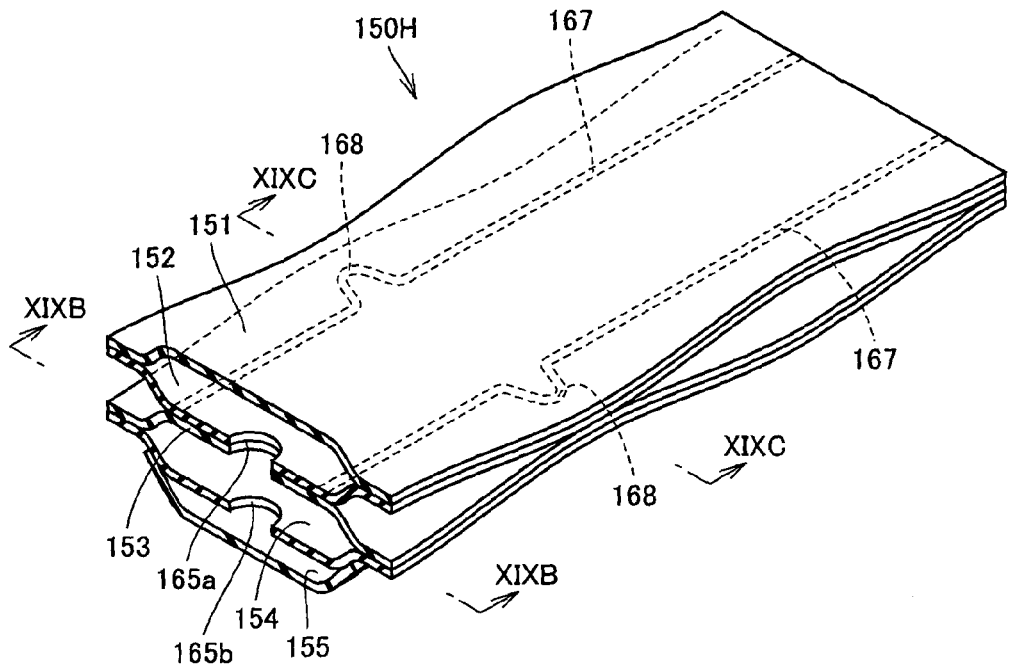
FIG. 19A is a schematic perspective view of an air bag contained in a cuff for a blood pressure monitor according to Example 8 based on the present embodiment, with a part of the air bag being cut out.
Figure 19B:
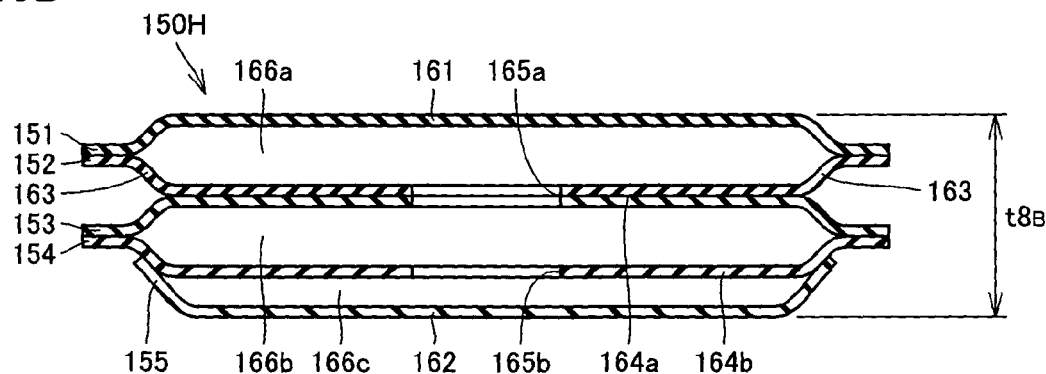
FIG. 19B is a schematic cross sectional view taken along the line XIXB-XIXB in FIG. 19A.
Figure 19C:
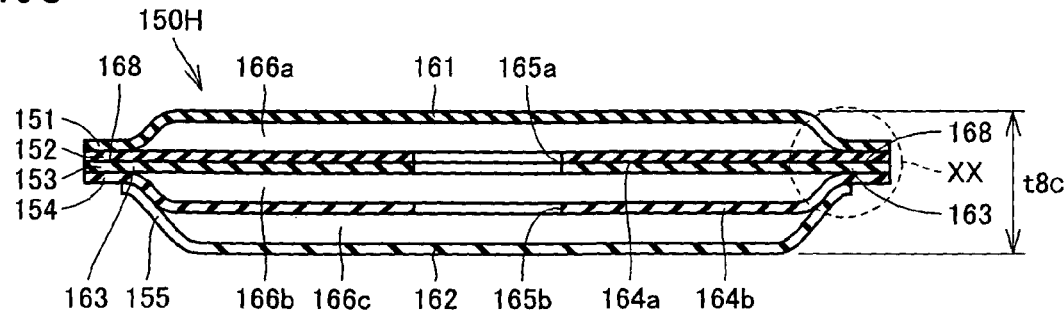
FIG. 19C is a schematic cross sectional view taken along the line XIXC-XIXC in FIG. 19A.
Figure 20:
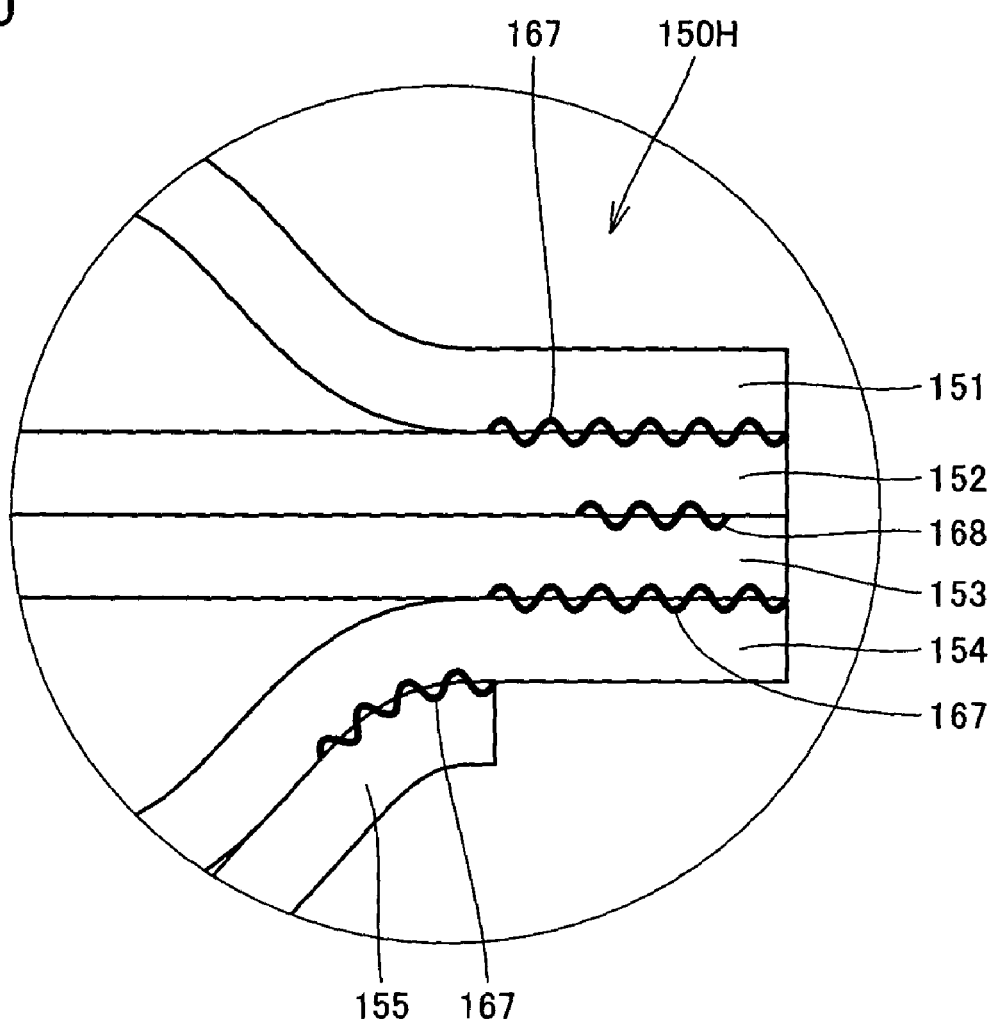
FIG. 20 is an enlarged view of a region XX shown in FIG. 19C.

FIG. 19A is a schematic perspective view of an air bag contained in a cuff for a blood pressure monitor according to Example 8 based on the present embodiment, with a part of the air bag being cut out. FIG. 19B is a schematic cross sectional view taken along the line XIXB-XIXB in FIG. 19A, and FIG. 19C is a schematic cross sectional view taken along the line XIXC-XIXC in FIG. 19A. FIG. 20 is an enlarged view of a region XX shown in FIG. 19C. The portions identical to those of air bag 150D of the cuff for a blood pressure monitor of Example 4 have the same reference characters allotted, and description thereof will not be repeated.

As shown in FIGS. 19A-19C, the air bag 150H of the cuff for a blood pressure monitor of the present example is formed into a bag shape using five resin sheets 151, 152, 153, 154 and 155, as in the case of air bag 150D of the cuff for a blood pressure monitor of Example 4 described above. Further, in air bag 150H of the cuff for a blood pressure monitor of the present example, a bonded portion 168, identified as a joined portion for reducing expansion of the gusset formed by side wall portion 163, is provided at a region of air bag 150H in its winding direction around the living body (i.e., the longitudinal direction of air bag 150H). This bonded portion 168 is formed as follows. Of the five resin sheets forming air bag 150H, resin sheets 151, 152 form the first bag, and resin sheets 153, 154 form the second bag, and the first and second bags are joined by melting and bonding resin sheets 152 and 153. Bonded portion 168 is formed by melting and bonding these resin sheets 152 and 153. More specifically, a part of a bonded portion 167 for connecting the first and second bag members, extending in the longitudinal direction of air bag 150H, is shifted outwards to approach the side end portion of air bag 150H to form bonded portion 168.

As shown in FIG. 20, bonded portion 168 is distinguished from a bonded portion 167 for sealing air bag 150H in an airtight manner. In air bag 150H of the cuff for a blood pressure monitor of the present example, wall surfaces of side wall portion 163 forming the gusset that would face each other when side wall portion 163 is folded, are melted and bonded to form bonded portion 168.

With this configuration, in the state where air bag 150H as a single body is inflated, as shown in FIGS. 19B and 19C, the thickness in the longitudinal direction of air bag 150H becomes uneven, with the region provided with bonded portion 168 having a thickness smaller than that of the other region when inflated. That is, the thickness $t8_C$ of the region provided with bonded portion 168 when inflated is smaller than the thickness $t8_B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width. Further, in air bag 150H of the cuff for a blood pressure monitor of the present example, the bonded portion identified as the joined portion for reducing expansion of the gusset formed by the side wall portion can be formed at the same time as the melting and bonding process for sealing the first and second bag members in an airtight manner. This simplifies the fabrication operation.

Furthermore, in air bag 150H of the cuff for a blood pressure monitor of the present example as well, bonded portion 168 for reducing expansion of the gusset formed by side wall portion 163 is preferably arranged approximately at a central portion in the winding direction of air bag 150H around the living body, for the same reasons as in the case of air bag 150A of the cuff for a blood pressure monitor of Example 1 described above.

Example 9

Figure 21A:
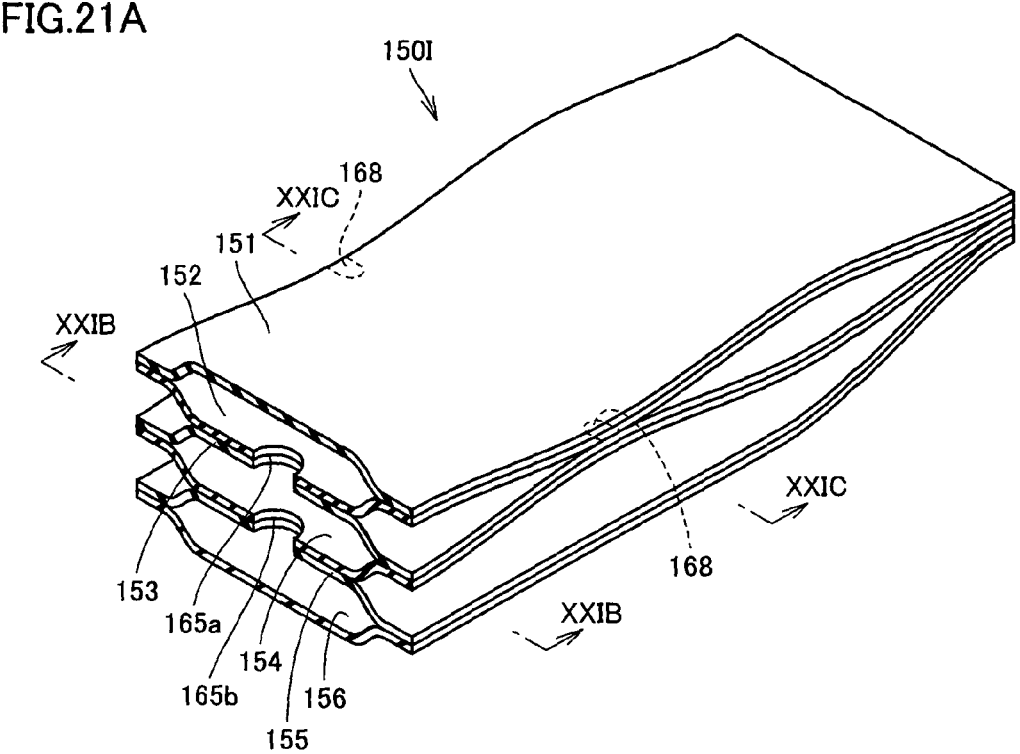
FIG. 21A is a schematic perspective view of an air bag contained in a cuff for a blood pressure monitor according to Example 9 based on the present embodiment, with a part of the air bag being cut out.
Figure 21B:
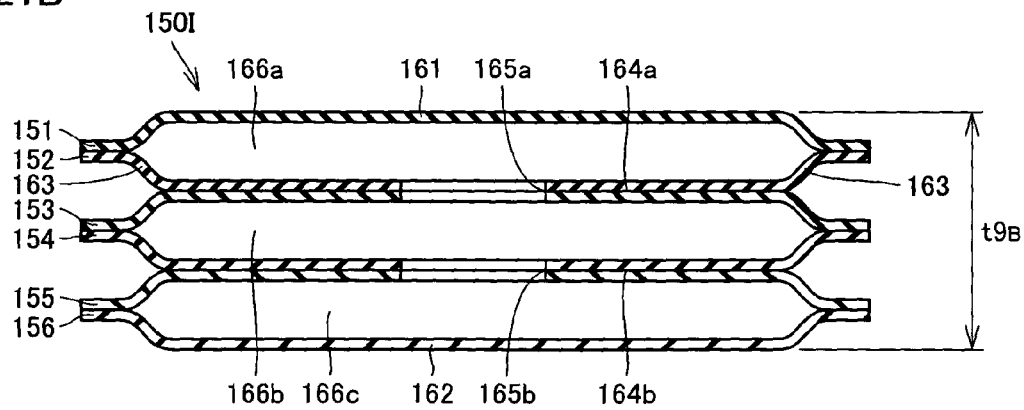
FIG. 21B is a schematic cross sectional view taken along the line XXIB-XXIB in FIG. 21A.
Figure 21C:
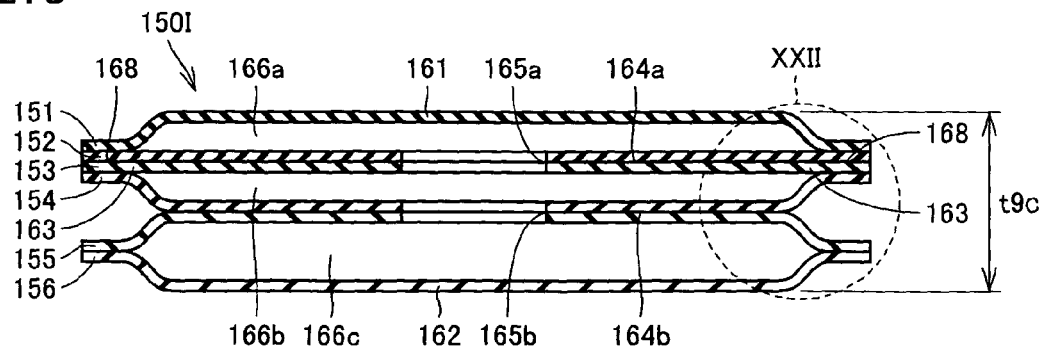
FIG. 21C is a schematic cross sectional view taken along the line XXIC-XXIC in FIG. 21A.
Figure 22:
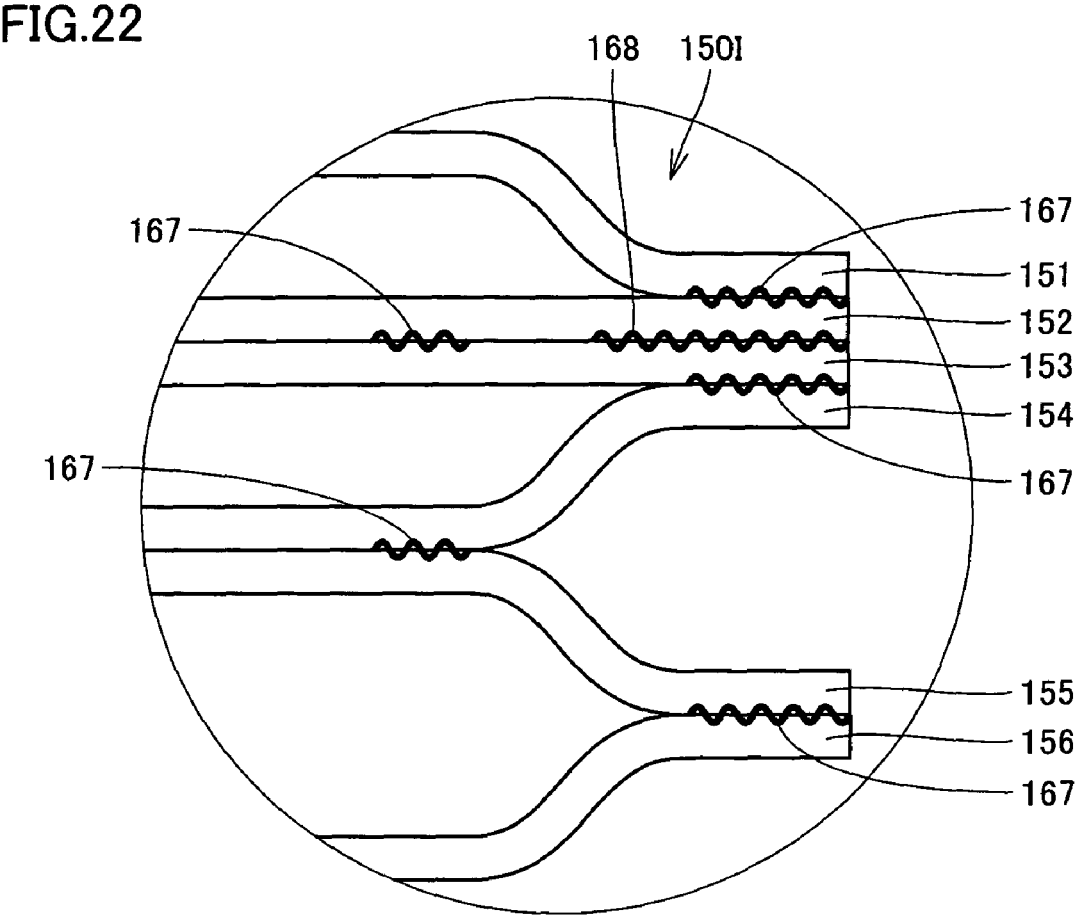
FIG. 22 is an enlarged view of a region XXII shown in FIG. 21C.

FIG. 21A is a schematic perspective view of an air bag contained in a cuff for a blood pressure monitor according to Example 9 based on the present embodiment, with a part of the air bag being cut out. FIG. 21B is a schematic cross sectional view taken along the line XXIB-XXIB in FIG. 21A, and FIG. 21C is a schematic cross sectional view taken along the line XXIC-XXIC in FIG. 21A. FIG. 22 is an enlarged view of a region XXII shown in FIG. 21C.

As shown in FIGS. 21A-21C, the air bag 150I of the cuff for a blood pressure monitor of the present example is formed into a bag shape using six resin sheets 151, 152, 153, 154, 155 and 156. More specifically, two resin sheets 151, 152 of an approximately rectangular shape in two dimensions are laid one on the other and their rims are melted and bonded to form a first bag member having a first inflated/deflated space 166a therein. Two resin sheets 153, 154 of an approximately rectangular shape in two dimensions are laid one on the other and their rims are melted and bonded to form a second bag member having a second inflated/deflated space 166b therein. Further, two resin sheets 155, 156 of an approximately rectangular shape in two dimensions are laid one on the other and their rims are melted and bonded to form a third bag member having a third inflated/deflated space 166c therein. The first, second and third bag members are laid one on another and melted and bonded at prescribed sites to thereby form an integrated bag member of three layers having first, second and third inflated/deflated spaces 166a, 166b and 166c. Of the six resin sheets, two resin sheets 152, 153 located in the region where the first and second bag members are connected have holes bored in advance at prescribed positions corresponding to each other, which constitute a communication hole 165a through which first inflated/deflated space 166a and second inflated/deflated space 166b communicate with each other after formation of air bag 150I. Further, of the six resin sheets, two resin sheets 154, 155 located in the region where the second and third bag members are connected have holes bored in advance at prescribed positions corresponding to each other, which constitute a communication hole 165b through which second inflated/deflated space 166b and third inflated/deflated space 166c communicate with each other after formation of air bag 150I.

Resin sheet 156 constitutes an inner wall portion 162 located on an inner side in the state where cuff 130 for a blood pressure monitor is mounted on the wrist. Resin sheet 151 constitutes an outer wall portion 161 located on an outer side than inner wall portion 162 in the state where cuff 130 is mounted on the wrist. Further, the respective side end portions in the width direction of resin sheets 152, 153, 154, 155 constitute side wall portions 163 for connecting inner wall portion 162 and outer wall portion 161. The side end portions in the width direction of resin sheets 152, 153, 154, 155 constituting side wall portions 163 of air bag 150I function as the gussets, as in the case of the side wall portions of air bag 150A of the cuff for a blood pressure monitor of Example 1 described above.

Further, resin sheets 152, 153 constitute a connecting portion 164a located between outer wall portion 161 and inner wall portion 162 inside air bag 150I, and connecting a pair of side wall portions 163 located at the respective side end portions of air bag 150I. Further, resin sheets 154, 155 constitute a connecting portion 164b located between outer wall portion 161 and inner wall portion 162 inside air bag 150I, and connecting a pair of side wall portions 163 located at the respective side end portions of air bag 150I. Connecting portions 164a, 164b are for guiding side wall portions 163 serving as the gussets to be surely folded inwards when air bag 150I changes from the inflated state to the deflated state.

As shown in FIGS. 21A-21C, in air bag 150I of the cuff for a blood pressure monitor of the present example, a bonded portion 168, identified as a joined portion for reducing expansion of the gusset formed by side wall portion 163, is provided at a region of air bag 150I in its winding direction around the living body (i.e., the longitudinal direction of air bag 150I). A pair of bonded portions 168 are provided at the respective side end portions in the width direction of air bag 150I.

As shown in FIG. 22, bonded portion 168 is distinguished from a bonded portion 167 for sealing air bag 150I in an airtight manner. In air bag 150I of the cuff for a blood pressure monitor of the present example, bonded portion 168 is formed in the following manner. Of the wall surfaces of side wall portion 163 that would face one another in the state where side wall portion 163 forming the gusset is folded, the wall surfaces formed by resin sheets 152 and 153 are melted and bonded to form bonded portion 168, as shown in FIG. 22.

With this configuration, in the state where air bag 150I as a single body is inflated, as shown in FIGS. 21B and 21C, the thickness in the longitudinal direction of air bag 150I becomes uneven, with the region provided with bonded portion 168 having a thickness smaller than that of the other region when inflated. That is, the thickness $t9_C$ of the region provided with bonded portion 168 when inflated is smaller than the thickness $t9_B$ of the region not provided with bonded portion 168 when inflated.

Accordingly, as in the case of Example 1, it is possible to provide a cuff that can press a measurement site uniformly in the width direction of the air bag, while preventing lateral displacement of the air bag, to reliably press the artery located beneath the skin of the measurement site for avascularization. As such, high avascularization performance is obtained even if the cuff is narrowed in width.

Furthermore, in air bag 150I of the cuff for a blood pressure monitor of the present example, as in the case of air bag 150A of the cuff for a blood pressure monitor of Example 1 described above, bonded portion 168 for reducing expansion of the gusset formed by side wall portion 163 is preferably arranged approximately at a central portion in the winding direction of air bag 150I around the living body. With this configuration, it is possible to effectively suppress occurrence of lateral displacement, and also minimize an adverse effect of degradation of avascularization performance attributable to provision of bonded portion 168.

Further, in air bag 150I of the cuff for a blood pressure monitor according to the present example, bonded portion 168 restricts expansion of only first and second inflated/deflated spaces 166a and 166b located outside among first through third inflated/deflated spaces 166a, 166b, 166c laid one on another in the thickness direction, as described above, and thus, other inflated/deflated space 166c expands sufficiently. Accordingly, air bag 150I can press the portion of the wrist where the tendon is located to some extent when inflated, which avoids deterioration of the avascularization performance.

In the present example, explanation was made about the case where a part of side wall portion 163 located at each side end portion in the width direction of air bag 150I is melted and bonded to reduce expansion of the gusset formed by side wall portion 163. However, in the case of the air bag having a multi-layered air bag structure formed of a plurality of resin sheets laid one on another to have a plurality of layers of inflated/deflated spaces, as in the case of the present example, a joined portion distinguished from the joined portion for sealing the inflated/deflated space in an airtight manner may be provided at a location on an inner side of the joined portion for sealing, so as to prevent lateral displacement. That is, a part of the connecting portion formed inside the air bag may be joined to another site of the air bag to prevent displacement of the joined resin sheets and, thus, to prevent lateral displacement. In this case, the joined portion for preventing displacement may be connected to the joined portion for sealing the inflated/deflated space, from the inner side in the width direction of the air bag. Alternatively, the joined portion for preventing displacement may be provided independently of the joined portion for sealing the inflated/deflated space. Further, the joined portion for preventing displacement does not necessarily have to be formed by connecting the resin sheet constituting the connecting portion to the resin sheet constituting the outer or inner wall portion. Alternatively, the resin sheets constituting the connecting portion(s) may be joined together to form the joined portion.

Example 10

Figure 23A:
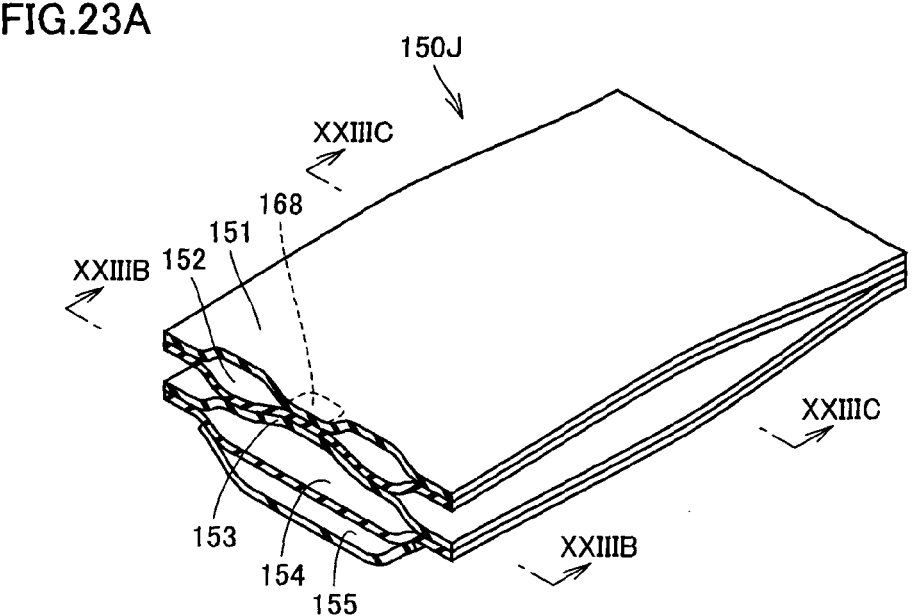
FIG. 23A is a schematic perspective view of an air bag contained in a cuff for a blood pressure monitor according to Example 10 based on the present embodiment, with a part of the air bag being cut out.
Figure 23B:
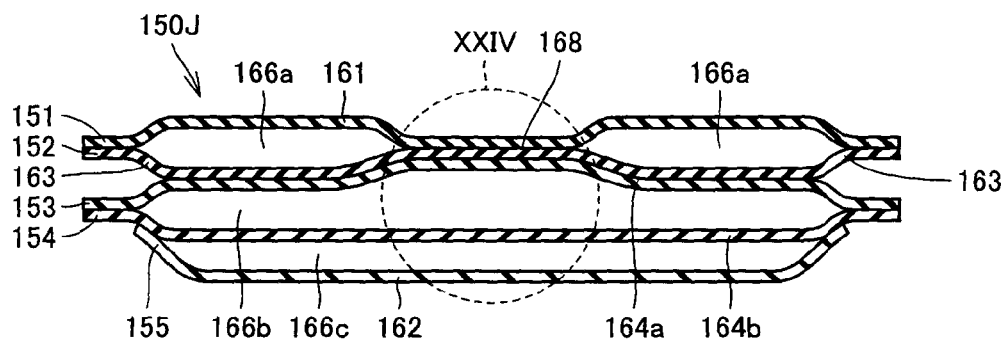
FIG. 23B is a schematic cross sectional view taken along the line XXIIIB-XXIIIB in FIG. 23A.
Figure 23C:
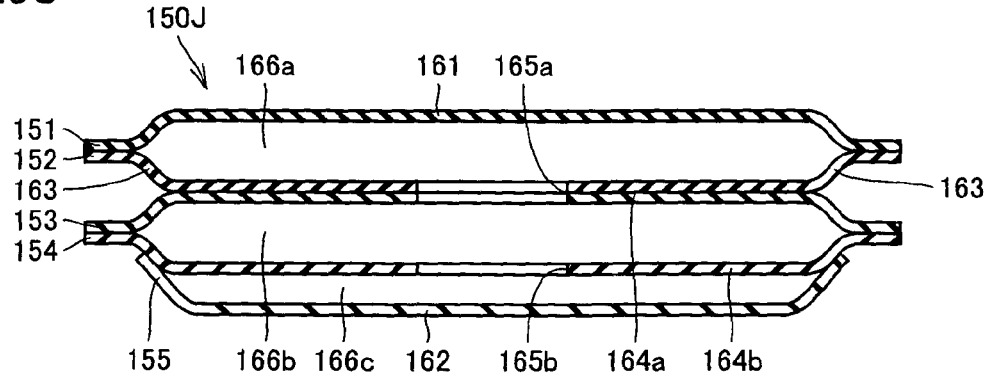
FIG. 23C is a schematic cross sectional view taken along the line XXIIIC-XXIIIC in FIG. 23A.
Figure 24:
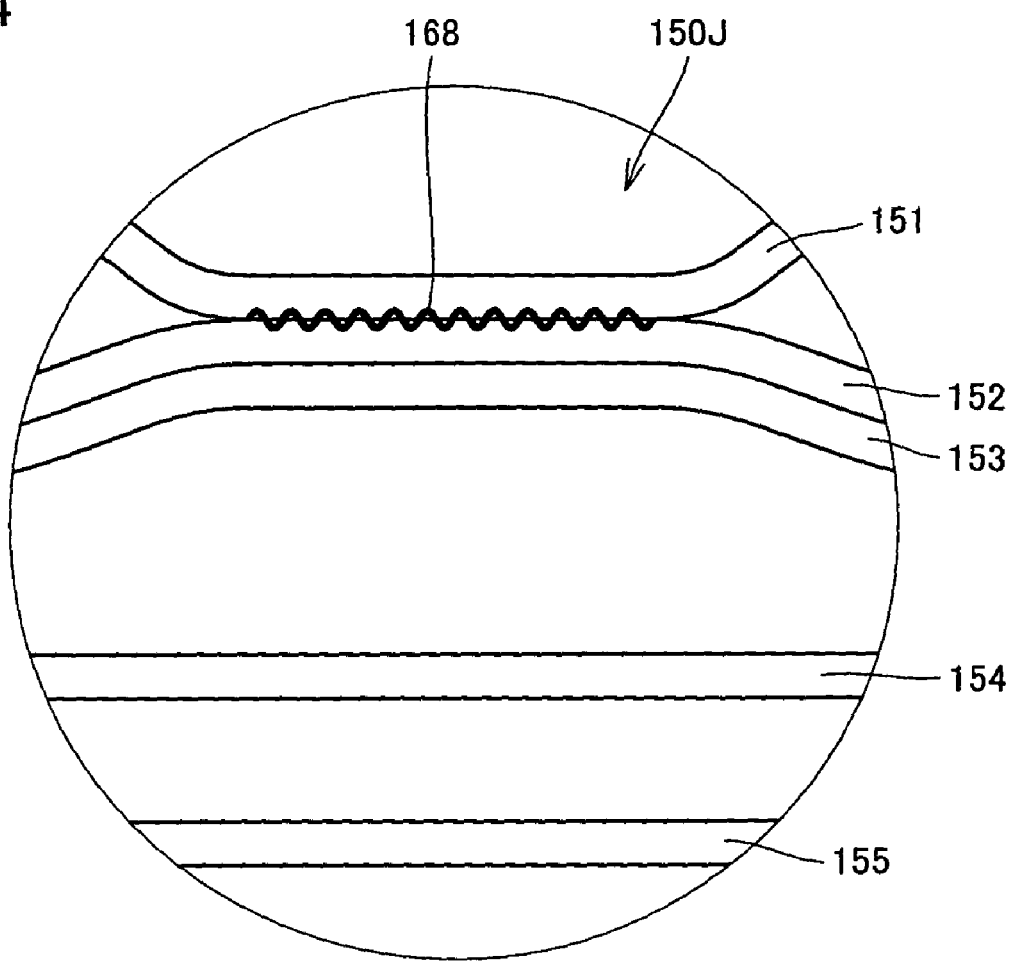
FIG. 24 is an enlarged view of a region XXIV shown in FIG. 23B.

FIG. 23A is a schematic perspective view of an air bag contained in a cuff for a blood pressure monitor according to Example 10 based on the present embodiment, with a part of the air bag being cut out. FIG. 23B is a schematic cross sectional view taken along the line XXIIIB-XXIIIB in FIG. 23A, and FIG. 23C is a schematic cross sectional view taken along the line XXIIIC-XXIIIC in FIG. 23A. FIG. 24 is an enlarged view of a region XXIV shown in FIG. 23B. The portions identical to those of air bag 150D of the cuff for a blood pressure monitor of Example 4 have the same reference characters allotted, and description thereof will not be repeated.

As shown in FIGS. 23A-23C, the air bag 150J of the cuff for a blood pressure monitor of the present example is formed into a bag shape using five resin sheets 151, 152, 153, 154 and 155, as in the case of air bag 150D of the cuff for a blood pressure monitor of Example 4 described above. Further, in air bag 150J of the cuff for a blood pressure monitor of the present example, a bonded portion 168 is provided at a region in the longitudinal direction of air bag 150J, which is formed by melting and bonding the wall surface of outer wall portion 161 with the wall surface of connecting portion 164a. Bonded portion 168 is provided approximately at a central portion in the width direction of air bag 150J.

Bonded portion 168 is distinguished from a bonded portion for sealing air bag 150J in an airtight manner. As shown in FIG. 24, in air bag 150J of the cuff for a blood pressure monitor of the present example, two resin sheets 151, 152 forming the first bag member are melted and bonded to form bonded portion 168.

With this configuration, in the state where air bag 150J is inflated, displacement between outer wall portion 161 and connecting portion 164a in the width direction of air bag 150J is unlikely to occur, whereby lateral displacement of air bag 150J is prevented. Further, the measurement site can be pressed uniformly in the width direction of air bag 150J, and thus, the artery located beneath the skin of the measurement site can be pressed reliably for avascularization. Thus, high avascularization performance can be obtained even if the cuff is narrowed in width.

Furthermore, in air bag 150J of the cuff for a blood pressure monitor of the present example as well, bonded portion 168 for preventing lateral displacement is preferably arranged approximately at a central portion in the longitudinal direction of air bag 150J, for the same reasons as in the case of air bag 150A of the cuff for a blood pressure monitor of Example 1 described above.

Example 11

Figure 25A:
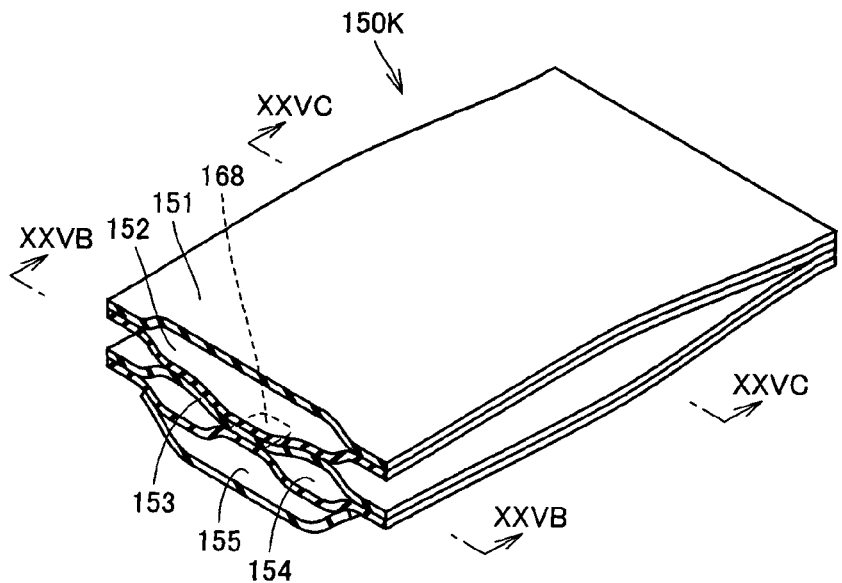
FIG. 25A is a schematic perspective view of an air bag contained in a cuff for a blood pressure monitor according to Example 11 based on the present embodiment, with a part of the air bag being cut out.
Figure 25B:
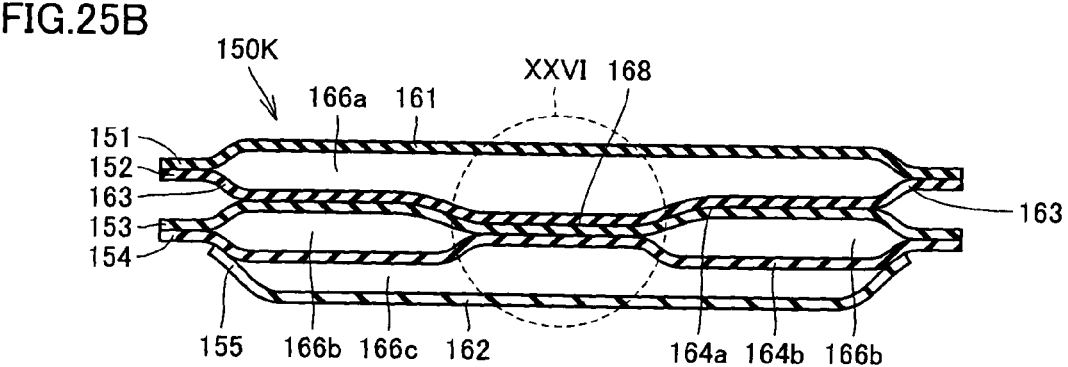
FIG. 25B is a schematic cross sectional view taken along the line XXVB-XXVB in FIG. 25A.
Figure 25C:
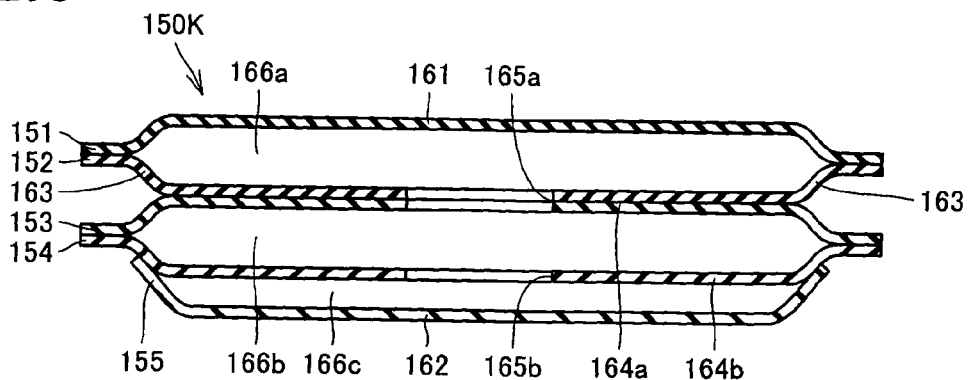
FIG. 25C is a schematic cross sectional view taken along the line XXVC-XXVC in FIG. 25A.
Figure 26:
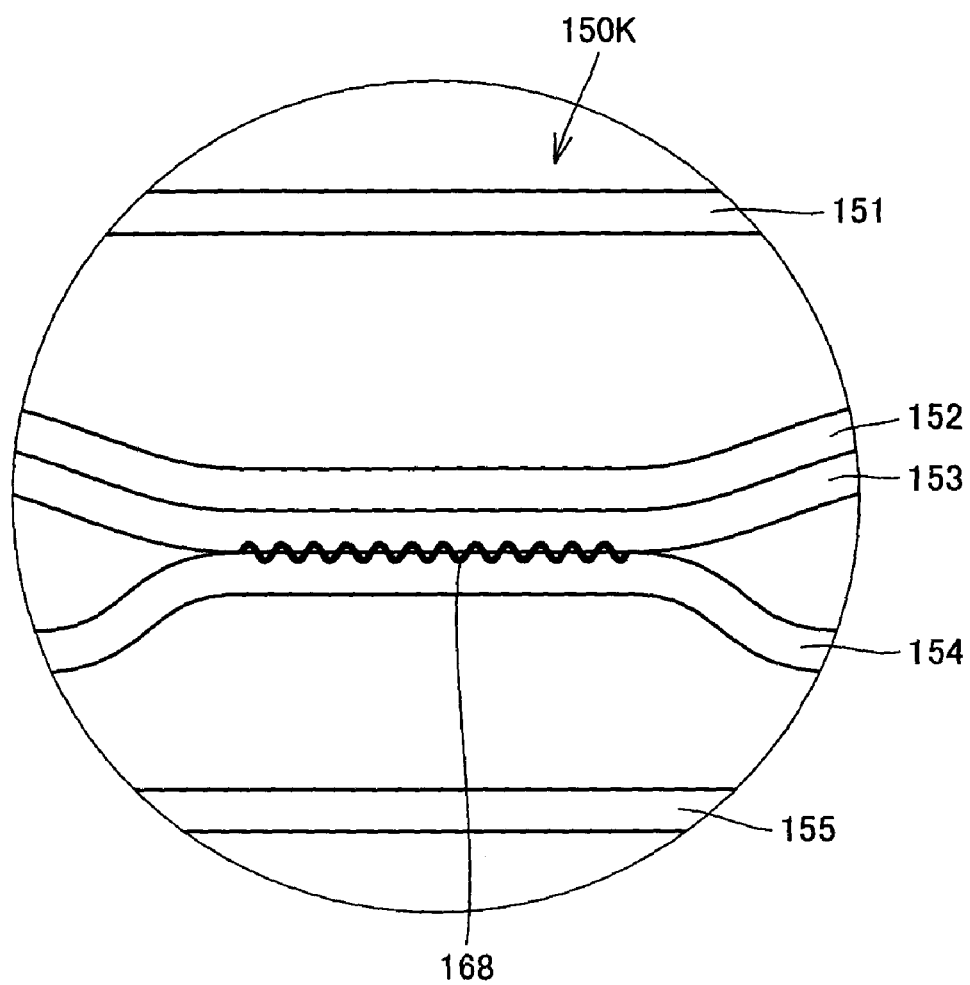
FIG. 26 is an enlarged view of a region XXVI shown in FIG. 25B.
Figure 27:
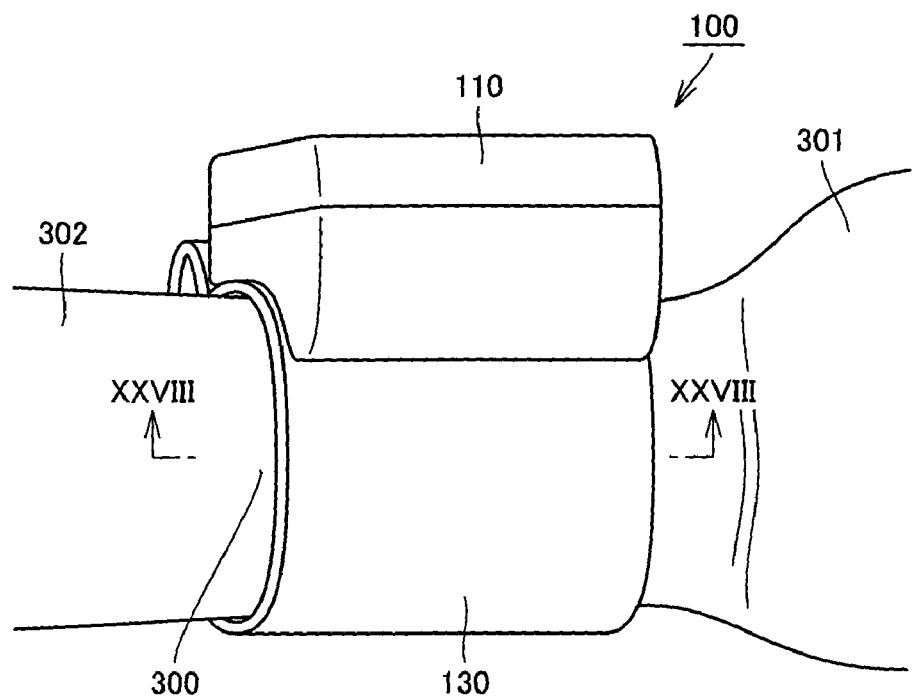
FIG. 27 is a schematic diagram showing the state where a typical wrist blood pressure monitor is mounted on a measurement site of the wrist.
Figure 28:
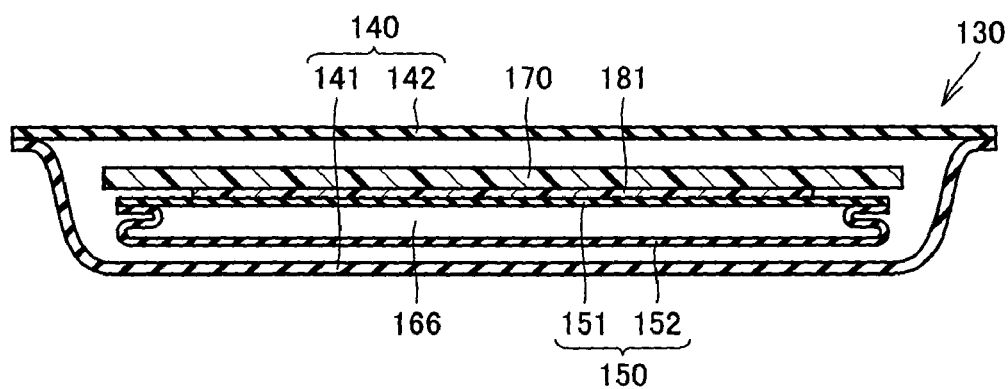
FIG. 28 is a schematic cross sectional view of the cuff for the blood pressure monitor shown in FIG. 27, taken along the line XXVIII-XXVIII in FIG. 27.
Figure 29:
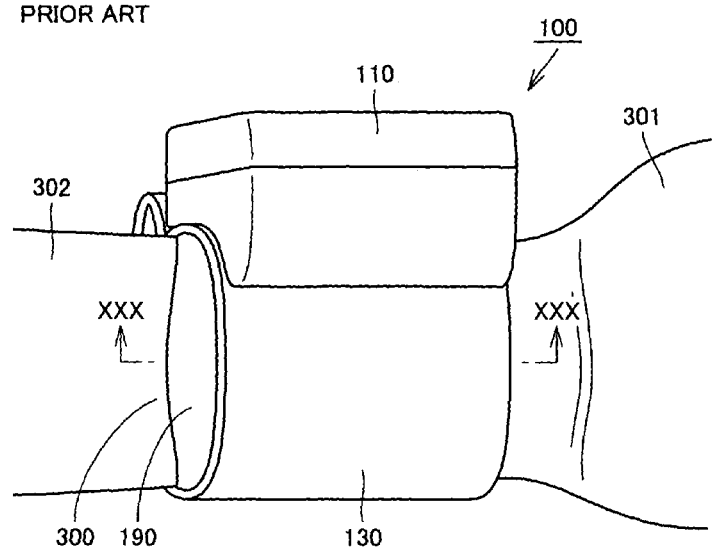
FIG. 29 is a schematic diagram showing the state where there occurs lateral displacement in the cuff for the wrist blood pressure monitor in the measurement state shown in FIG. 27.
Figure 30:
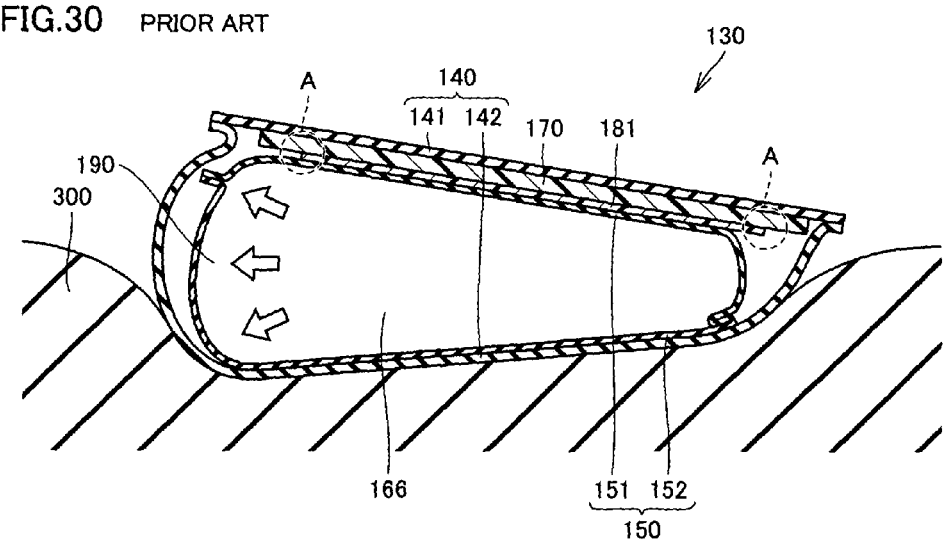
FIG. 30 is a schematic cross sectional view of the cuff for a blood pressure monitor and the wrist shown in FIG. 29, taken along the line XXX-XXX in FIG. 29.

FIG. 25A is a schematic perspective view of an air bag contained in a cuff for a blood pressure monitor according to Example 11 based on the present embodiment, with a part of the air bag being cut out. FIG. 25B is a schematic cross sectional view taken along the line XXVB-XXVB in FIG. 25A, and FIG. 25C is a schematic cross sectional view taken along the line XXVC-XXVC in FIG. 25A. FIG. 26 is an enlarged view of a region XXVI shown in FIG. 25B. The portions identical to those of air bag 150J of the cuff for a blood pressure monitor of Example 10 have the same reference characters allotted, and description thereof will not be repeated.

As shown in FIGS. 25A-25C, the air bag 150K of the cuff for a blood pressure monitor of the present example is formed into a bag shape using five resin sheets 151, 152, 153, 154 and 155, as in the case of air bag 150J of the cuff for a blood pressure monitor of Example 10 described above. Further, in air bag 150K of the cuff for a blood pressure monitor of the present example, a bonded portion 168 is provided at a region in the longitudinal direction of air bag 150K, which is formed by melting and bonding the wall surface of connecting portion 164a with the wall surface of connecting portion 164b. Bonded portion 168 is provided approximately at a central portion in the width direction of air bag 150K.

Bonded portion 168 is distinguished from a bonded portion for sealing air bag 150K in an airtight manner. As shown in FIG. 26, in air bag 150K of the cuff for a blood pressure monitor of the present example, two resin sheets 153, 154 forming the second bag member are melted and bonded to form bonded portion 168.

With this configuration, in the state where air bag 150K is inflated, displacement between connecting portion 164a and connecting portion 164b in the width direction of air bag 150K is unlikely to occur, whereby lateral displacement of air bag 150K is prevented. Further, the measurement site can be pressed uniformly in the width direction of air bag 150K, and thus, the artery located beneath the skin of the measurement site can be pressed reliably for avascularization. Thus, high avascularization performance can be obtained even if the cuff is narrowed in width.

Furthermore, in air bag 150K of the cuff for a blood pressure monitor of the present example as well, bonded portion 168 for preventing lateral displacement is preferably arranged approximately at a central portion in the longitudinal direction of air bag 150K, for the same reasons as in the case of air bag 150A of the cuff for a blood pressure monitor of Example 1 described above.

In the embodiment described above, the case of joining the resin sheets all by melting and bonding was explained. However, the joining does not necessarily have to be carried out by melting and bonding. It is of course possible to employ another joining method such as adhesion using an adhesive or the like.

Further, in the embodiment described above, the case of using a double-faced tape to attach the curled elastic member to the air bag was explained by way of example. However, they do not necessarily have to be secured by attachment. They may be secured by another method, or they may be left completely unfixed to each other.

Furthermore, in the embodiment described above, the case of forming the air bag by laying a plurality of resin sheets one on another and melting and bonding the same was explained by way of example. However, it does not necessarily have to be formed using a plurality of resin sheets. The air bag may be formed using a single sheet of a cylindrical shape, and the present invention is applicable to such a case as well.

In the embodiment described above, the case of applying the present invention to a cuff for use in a wrist blood pressure monitor assuming the wrist as the measurement site was explained by way of example. However, not limited thereto, the present invention is applicable to a cuff for any type of blood pressure monitor, including an upper arm type and a finger type.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A cuff for a blood pressure monitor having a fluid bag inflated and deflated as a fluid comes in and out, wherein
    said fluid bag includes an inner wall portion located on an inner side in the state where the cuff for a blood pressure monitor is wound around a living body, an outer wall portion located on an outer side than said inner wall portion, a first side wall portion connecting a side end portion of said inner wall portion and a side end portion of said outer wall portion and folded inwards in a width direction of said fluid bag in a deflated state where said fluid bag is not pressurized to thereby form a gusset at a side end portion of said fluid bag, and a second side wall portion opposite the first side wall portion in the width direction of said fluid bag, and
    a joined portion for reducing expansion of the gusset formed by said first side wall portion is provided at a region of the side end portion of said fluid bag in its winding direction around the living body, wherein said joined portion does not join said first side wall portion to said second side wall portion.

2. The cuff for a blood pressure monitor according to claim 1, wherein said joined portion is formed by joining wall surfaces of said first side wall portion that would face each other in the state where said first side wall portion is folded.

3. The cuff for a blood pressure monitor according to claim 1, wherein said joined portion is formed by joining a wall surface of said first side wall portion with a wall surface of said outer wall portion that the wall surface of said first side wall portion would face in the state where said first side wall portion is folded.

4. The cuff for a blood pressure monitor according to claim 1, wherein said joined portion is formed by joining a wall surface of said first side wall portion with a wall surface of said inner wall portion that the wall surface of said first side wall portion would face in the state where said first side wall portion is folded.

5. The cuff for a blood pressure monitor according to claim 1, wherein said fluid bag further has a connecting portion located between said inner wall portion and said outer wall portion inside said fluid bag and connecting said first side wall portion and said second side wall portion.

6. The cuff for a blood pressure monitor according to claim 1, wherein said joined portion is located approximately at a central portion of said fluid bag in its winding direction around the living body.

7. The cuff for a blood pressure monitor according to claim 1, wherein joining in said joined portion is performed by melting and bonding.

8. A blood pressure monitor, comprising:
a cuff for a blood pressure monitor including a fluid bag inflated and deflated as a fluid comes in and out;
an inflating/deflating portion for inflating and deflating said fluid bag;
a pressure detecting portion for detecting a pressure in said fluid bag; and
a blood pressure value calculating portion for calculating a blood pressure value based on pressure information detected by said pressure detecting portion;

wherein
said fluid bag includes an inner wall portion located on an inner side in the state where said cuff for a blood pressure monitor is wound around a living body, an outer wall portion located on an outer side than said inner wall portion, a first side wall portion connecting a side end portion of said inner wall portion and a side end portion of said outer wall portion and folded inwards in a width direction of said fluid bag in a deflated state where said fluid bag is not pressurized to thereby form a gusset at a side end portion of said fluid bag, and a second side wall portion opposite the first side wall portion in the width direction of said fluid bag, and
a joined portion for reducing expansion of the gusset formed by said first side wall portion is provided at a region of the side end portion of said fluid bag in its winding direction around the living body, wherein said joined portion does not join said first side wall portion to said second side wall portion.

* * * * *